United States Patent
Amanai

(10) Patent No.: US 11,079,588 B2
(45) Date of Patent: Aug. 3, 2021

(54) RELAY OPTICAL SYSTEM, AND OPTICAL SYSTEM FOR RIGID ENDOSCOPE AND RIGID ENDOSCOPE USING THE SAME

(71) Applicant: OLYMPUS CORPORATION, Hachioji (JP)

(72) Inventor: Takahiro Amanai, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 215 days.

(21) Appl. No.: 16/221,560

(22) Filed: Dec. 16, 2018

(65) Prior Publication Data
US 2019/0121116 A1 Apr. 25, 2019

Related U.S. Application Data

(63) Continuation of application No. PCT/JP2017/021080, filed on Jun. 7, 2017.

(30) Foreign Application Priority Data

Jun. 17, 2016 (WO) .................. PCT/JP2016/068168

(51) Int. Cl.
*G02B 23/24* (2006.01)
*A61B 1/07* (2006.01)
(Continued)

(52) U.S. Cl.
CPC ............ *G02B 23/243* (2013.01); *A61B 1/055* (2013.01); *A61B 1/0661* (2013.01); *A61B 1/07* (2013.01);
(Continued)

(58) Field of Classification Search
CPC .. G02B 23/243; G02B 13/00; G02B 13/0095; G02B 23/26; G02B 27/0056;
(Continued)

(56) References Cited

U.S. PATENT DOCUMENTS

| 4,693,568 A * | 9/1987 | Takahashi .......... A61B 1/00096 |
| | | 359/772 |
| 4,946,267 A | 8/1990 | Hoogland |

(Continued)

FOREIGN PATENT DOCUMENTS

| JP | 2003524204 A | 8/2003 |
| JP | 2015508511 A | 3/2015 |

(Continued)

OTHER PUBLICATIONS

International Preliminary Report on Patentability (IPRP) (and English language translation thereof) and Written Opinion dated Dec. 27, 2018 issued in counterpart International Application No. PCT/JP2017/021080.
(Continued)

*Primary Examiner* — Arnel C Lavarias
(74) *Attorney, Agent, or Firm* — Holtz, Holtz & Volek PC

(57) ABSTRACT

A relay optical system includes a cemented lens in which a first lens, a second lens, and a third lens having are cemented. The first lens is a meniscus lens which is adjacent to the third lens, and a dispersion and a partial dispersion ratio differ for the first lens and the third lens. In a rectangular coordinate system in which a horizontal axis is set to be vdLA and a vertical axis is set to be θgFLA, when a straight line expressed by θgFLA=α×vdLA+βLA (where, α=−0.00163) is set, θgFLA and vdLA of medium of the first lens are included in an area determined by the following conditional expression (1) and conditional expression (2), and the following conditional expression (3) is satisfied:

$$0.67 \leq \beta LA \quad (1)$$
$$vdLA < 50 \quad (2)$$
$$-1.4 < mg < -0.6 \quad (3).$$

18 Claims, 22 Drawing Sheets

(51) Int. Cl.
*G02B 23/26* (2006.01)
*A61B 1/055* (2006.01)
*A61B 1/06* (2006.01)
*G02B 13/00* (2006.01)
*G02B 27/00* (2006.01)

(52) U.S. Cl.
CPC ..... *G02B 13/0095* (2013.01); *G02B 23/2446* (2013.01); *G02B 23/2461* (2013.01); *G02B 23/26* (2013.01); *G02B 27/005* (2013.01)

(58) Field of Classification Search
CPC ................ G02B 23/2446; G02B 23/24; G02B 23/2407; A61B 1/055; A61B 1/0661; A61B 1/07; A61B 1/00163; A61B 1/00195; A61B 1/002; A61B 1/04
USPC ....... 359/434, 362, 363, 368, 435, 558, 566, 359/569, 576; 600/101, 109, 160, 162, 600/181
See application file for complete search history.

(56) References Cited

U.S. PATENT DOCUMENTS

| | | | | |
|---|---|---|---|---|
| 4,993,817 A | | 2/1991 | Hoogland | |
| 5,093,719 A | * | 3/1992 | Prescott | G02B 3/0087 348/65 |
| 5,142,410 A | * | 8/1992 | Ono | G02B 23/2446 359/434 |
| 5,568,312 A | | 10/1996 | Horton | |
| 5,651,759 A | * | 7/1997 | Leiner | A61B 1/00179 600/128 |
| 5,684,629 A | * | 11/1997 | Leiner | A61B 1/002 359/362 |
| 6,490,085 B1 | * | 12/2002 | Zobel | G02B 23/2446 359/435 |
| 7,002,741 B2 | * | 2/2006 | Lei | G02B 23/2446 359/362 |
| 7,515,335 B2 | * | 4/2009 | Tomioka | G02B 23/2446 359/434 |
| 2004/0125445 A1 | | 7/2004 | Hoogland | |
| 2013/0194667 A1 | | 8/2013 | Inoue | |
| 2014/0313578 A1 | | 10/2014 | Schouwink et al. | |
| 2014/0343362 A1 | | 11/2014 | Tesar | |

FOREIGN PATENT DOCUMENTS

| | | |
|---|---|---|
| JP | 2015118136 A | 6/2015 |
| WO | 8911112 A1 | 11/1989 |
| WO | 2013021704 A1 | 2/2013 |
| WO | 2014199236 A2 | 12/2014 |

OTHER PUBLICATIONS

International Search Report (ISR) dated Sep. 5, 2017 issued in International Application No. PCT/JP2017/021080.

Written Opinion dated Sep. 5, 2017 issued in International Application No. PCT/JP2017/021080.

* cited by examiner

RELAY OPTICAL SYSTEM, AND OPTICAL SYSTEM FOR RIGID ENDOSCOPE AND RIGID ENDOSCOPE USING THE SAME

CROSS-REFERENCE TO RELATED APPLICATION

The present application is a continuation application of International Application No. PCT/JP2017/021080 filed on Jun. 7, 2017, which is based upon and claims the benefit of priority from International Application No. PCT/JP2016/068168 filed on Jun. 17, 2016; the entire contents of which are incorporated herein by reference.

BACKGROUND OF THE INVENTION

Field of the Invention

The present invention relates to a relay optical system, and an optical system for rigid endoscope and a rigid endoscope using the same.

Description of the Related Art

In recent years, in a diagnosis using a rigid endoscope, an improvement in a diagnostic accuracy is sought. In order to fulfil this requirement, in the rigid endoscope, an ability to observe an object with a high resolution and an ability to acquire an image of the object with a high image quality have been sought.

An observation and an acquisition of the image of the object are carried out via an optical system for rigid endoscope disposed in the rigid endoscope. In the acquisition of the image of the object, a camera head for instance is connected to the optical system for rigid endoscope. In the camera head, a CCD (Charge Coupled Devices) or a CMOS (Complementary Metal Oxide Semiconductor) is used as an image pickup element.

The optical system for rigid endoscope includes an objective lens, an eyepiece, and a plurality of relay optical systems. The plurality of relay optical systems is disposed between the objective lens and the eyepiece.

An image of the object (hereinafter, referred to as 'primary image') is formed by the objective lens. The primary image becomes an inverted image, or in other words, becomes an image in which the object is inverted in a vertical direction. In a relay optical system, the primary image is relayed. An image formed by a relay optical system is also an inverted image. The primary image is an inverted image and an image relayed is also an inverted image. Therefore, an image, after being relayed once, becomes an erected image. In the rigid endoscope, usually, an erected image is to be observed or captured. The primary image being an inverted image, the number of relay optical system becomes odd.

In Japanese Patent Application Laid-open Publication No. 2015-508511, a relay optical system has been disclosed. The relay optical system includes two rod lenses and an achromatic lens. The achromatic lens is disposed between the rod lenses. In the relay optical system disclosed in Japanese Patent Application Laid-open Publication No. 2015-508511, by using an ED glass for the achromatic lens, an occurrence of a chromatic aberration is suppressed.

A plurality of relay optical systems is disposed in the optical system for rigid endoscope. In this case, a large portion of the optical system for rigid endoscope is occupied by the relay optical systems. Therefore, an imaging performance of the relay optical systems has an extremely significant effect on an imaging performance of the optical system for rigid endoscope.

For such reason, in a relay optical system, it becomes significant that various aberrations are corrected favorably. For realizing the observation of the object with high resolution and acquisition of an image of the object with a high image quality, it is preferable that the chromatic aberration be corrected favorably.

SUMMARY OF THE INVENTION

A relay optical system according to at least some embodiments of the present invention comprises:
a cemented lens in which a first lens having a positive refractive power, a second lens having a positive refractive power, and a third lens having a negative refractive power are cemented, wherein
the cemented lens is disposed in an optical path of the relay optical system, which is formed by an object-side optical path and an image-side optical path, and
the first lens is a meniscus lens which is adjacent to the third lens, and
a dispersion and a partial dispersion ratio differ for the first lens and the third lens, and
in a rectangular coordinate system in which a horizontal axis is let to be $vd_{LA}$ and a vertical axis is let to be $\theta gF_{LA}$,
when a straight line expressed by $\theta gF_{LA} = \alpha \times vd_{LA} + \beta_{LA}$ (where, $\alpha = -0.00163$) is set,
$\theta gF_{LA}$ and $vd_{LA}$ of a medium of the first lens are included in an area determined by the following conditional expression (1) and conditional expression (2), and the following conditional expression (3) is satisfied:

$$0.67 \leq \beta_{LA} \tag{1}$$

$$vd_{LA} < 50 \tag{2}$$

$$-1.4 < mg < -0.6 \tag{3}$$

where,
$\theta gF_{LA}$ denotes a partial dispersion ratio $(ng_{LA} - nF_{LA})/(nF_{LA} - nC_{LA})$ of the medium of the first lens,
$vd_{LA}$ denotes Abbe number $(nd_{LA} - 1)/(nF_{LA} - nC_{LA})$ for the medium of the first lens, and here
$nd_{LA}$, $nC_{LA}$, $nF_{LA}$, and $ng_{LA}$ are refractive indices of the medium of the first lens for a d-line, a C-line, an F-line, and a g-line respectively,
mg denotes a magnification of the relay optical system,
the object-side optical path is an optical path positioned on an object side of a center of the relay optical system, and
the image-side optical path is an optical path positioned on an image side of the center of the relay optical system.

An image relay unit according to at least some embodiments of the present invention comprises:
a plurality of relay optical systems, wherein
at least one relay optical system of the plurality of relay optical systems is the abovementioned relay optical system.

An optical system for rigid endoscope according to at least some embodiments of the present invention comprises:
an objective optical system, and
an image relay unit which is disposed on an image side of the objective optical system, wherein
the image relay unit is the abovementioned image relay unit.

A rigid endoscope according to at least some embodiments of the present invention comprises:

the abovementioned optical system for rigid endoscope, and an image pickup element which captures an image formed by the image relay unit.

A rigid endoscope according to at least some embodiments of the present invention comprises:

the abovementioned optical system for rigid endoscope, and an illuminating unit which illuminates an object to be observed.

DETAILED DESCRIPTION OF THE INVENTION

Figure 1:
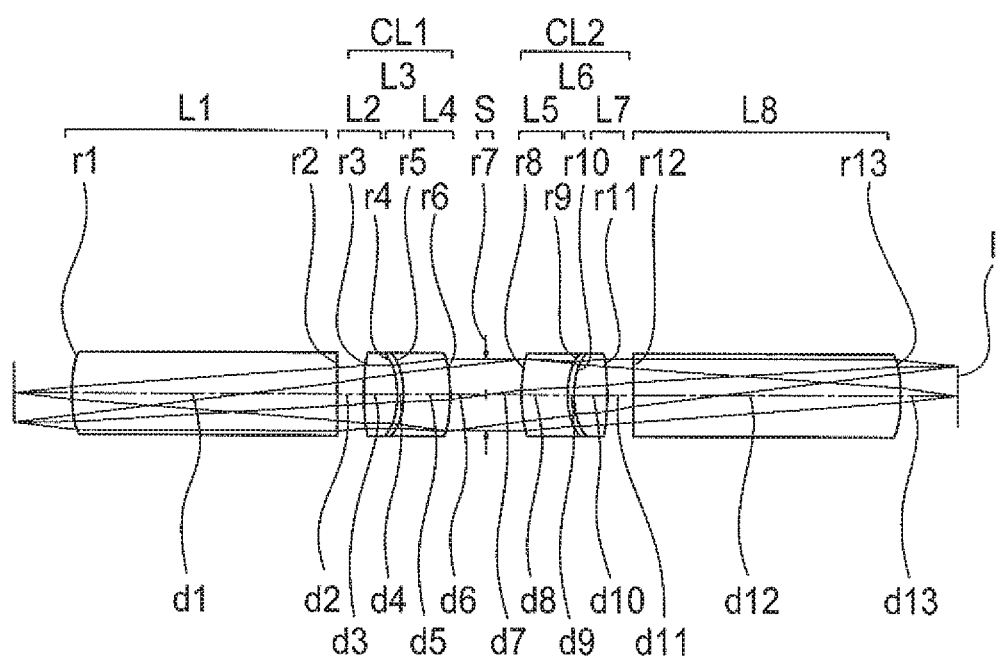
FIG. 1 is a lens cross-sectional view of a relay optical system of an example 1.
Figure 2:
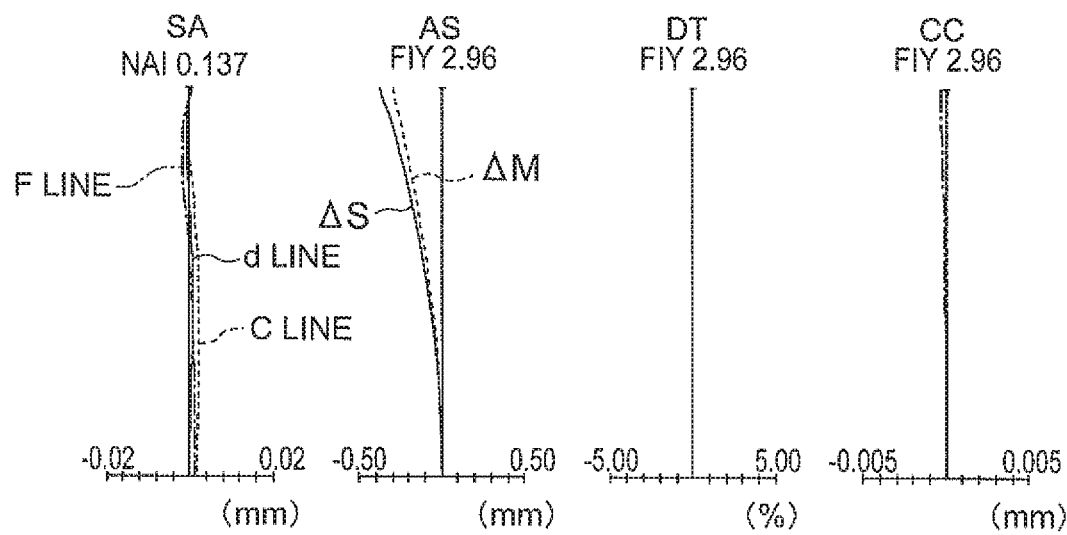
FIG. 2A, FIG. 2B, FIG. 2C, and FIG. 2D are aberration diagrams of the relay optical system of the example 1.
Figure 3:
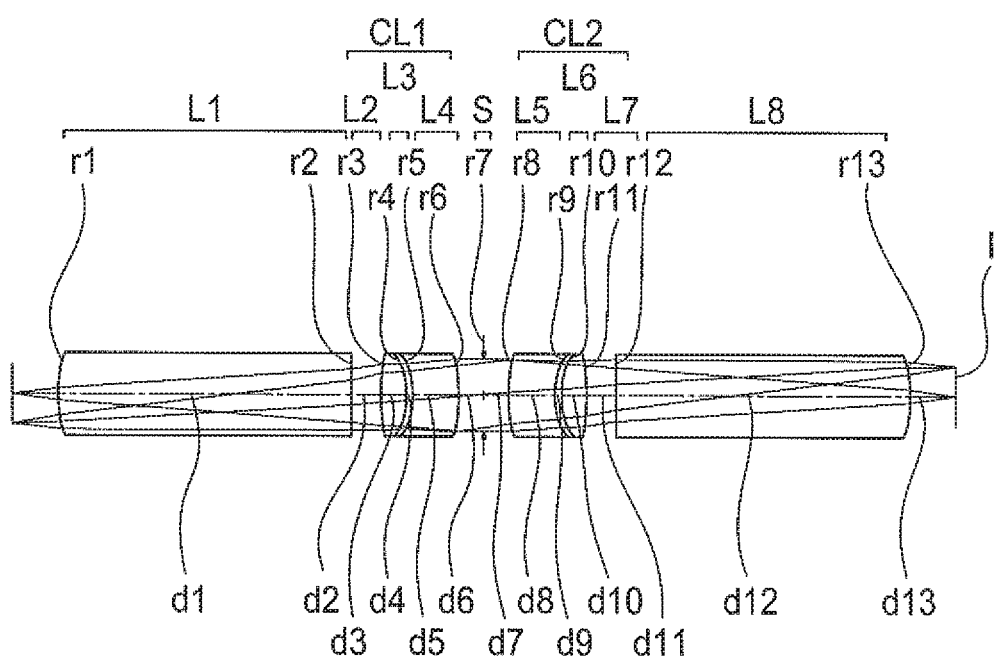
FIG. 3 is a lens cross-sectional view of a relay optical system of an example 2.
Figure 4:
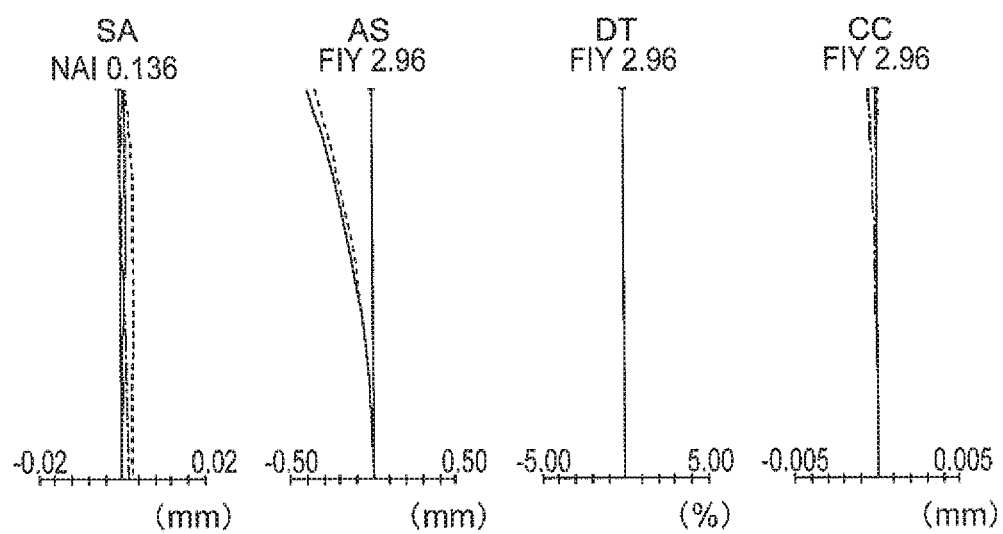
FIG. 4A, FIG. 4B, FIG. 4C, and FIG. 4D are aberration diagrams of the relay optical system of the example 2.
Figure 5:
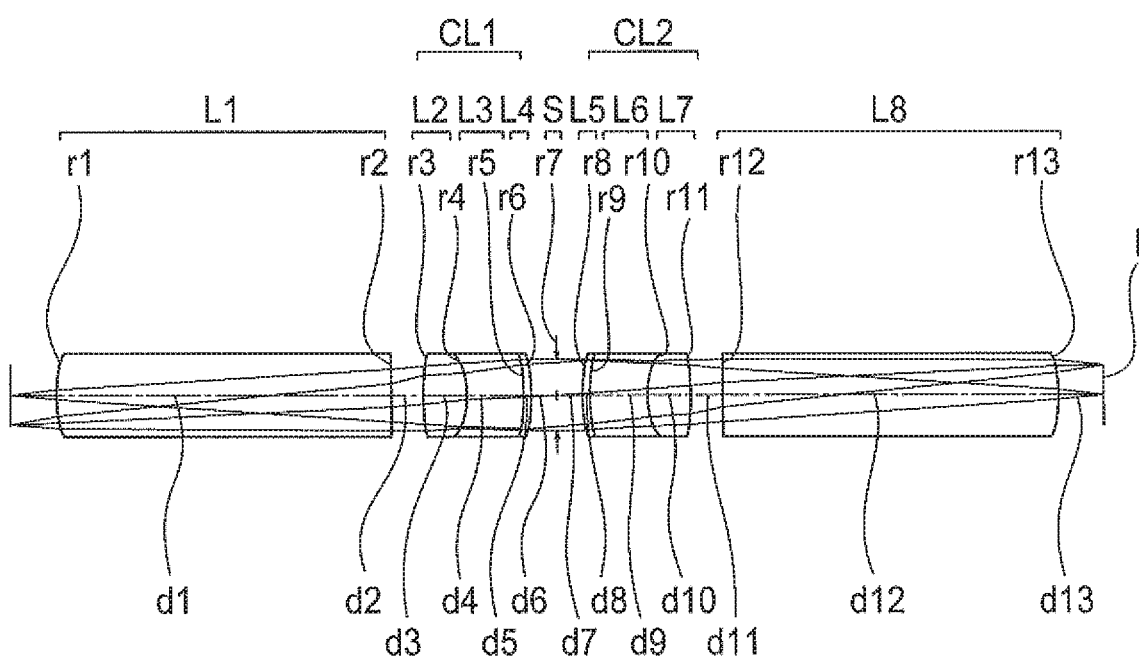
FIG. 5 is a lens cross-sectional view of a relay optical system of an example 3.
Figures 6A, 6B, 6C, 6D:
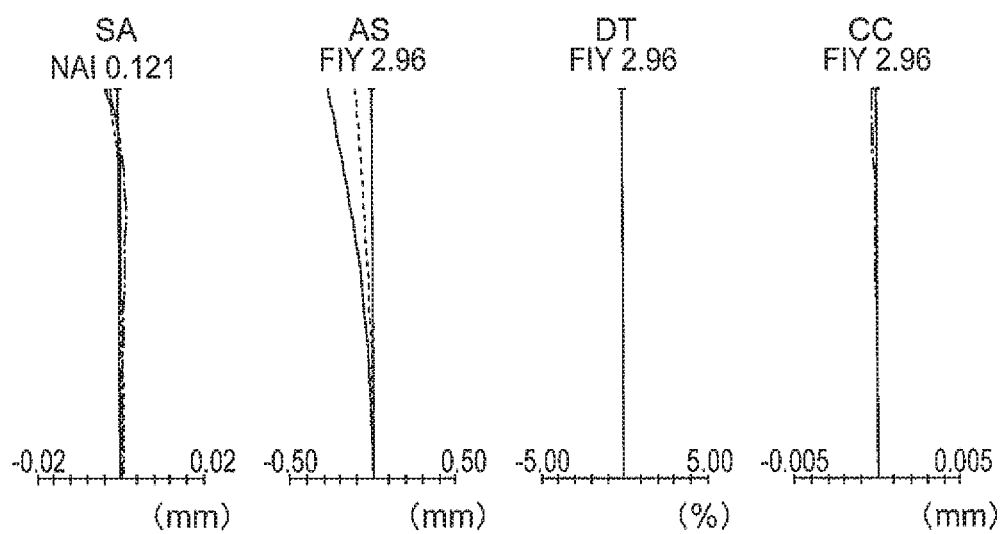
FIG. 6A, FIG. 6B, FIG. 6C, and FIG. 6D are aberration diagrams of the relay optical system of the example 3.
Figure 7:
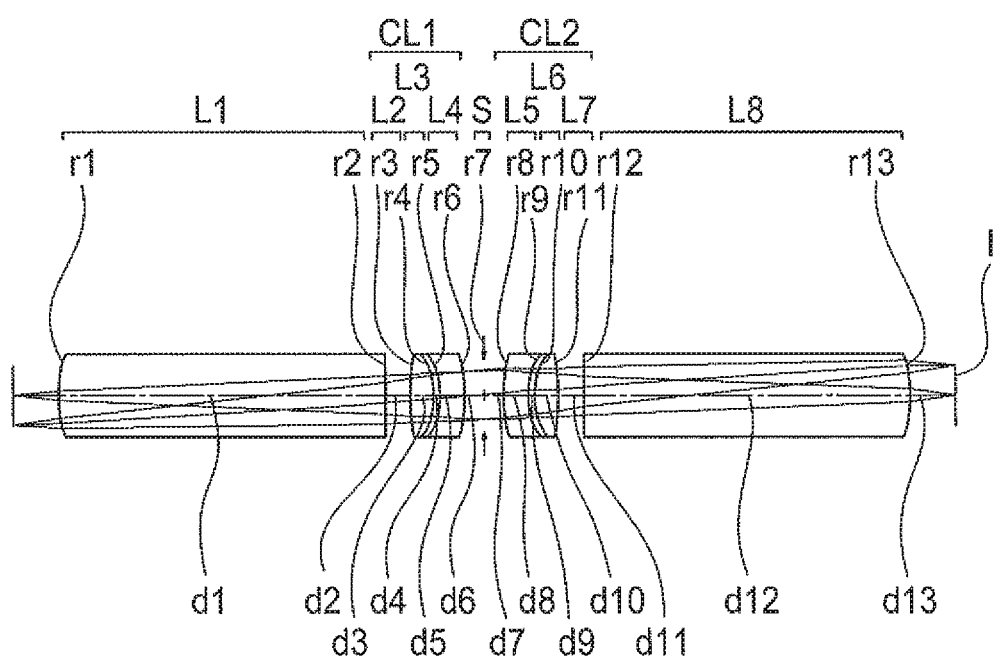
FIG. 7 is a lens cross-sectional view of a relay optical system of an example 4.
Figure 8:
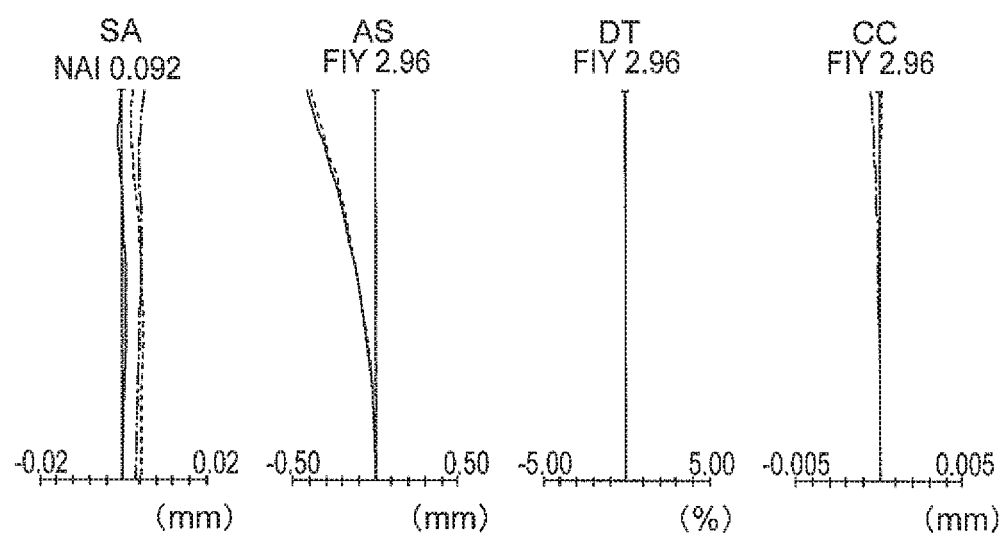
FIG. 8A, FIG. 8B, FIG. 8C, and FIG. 8D are aberration diagrams of the relay optical system of the example 4.
Figure 9:
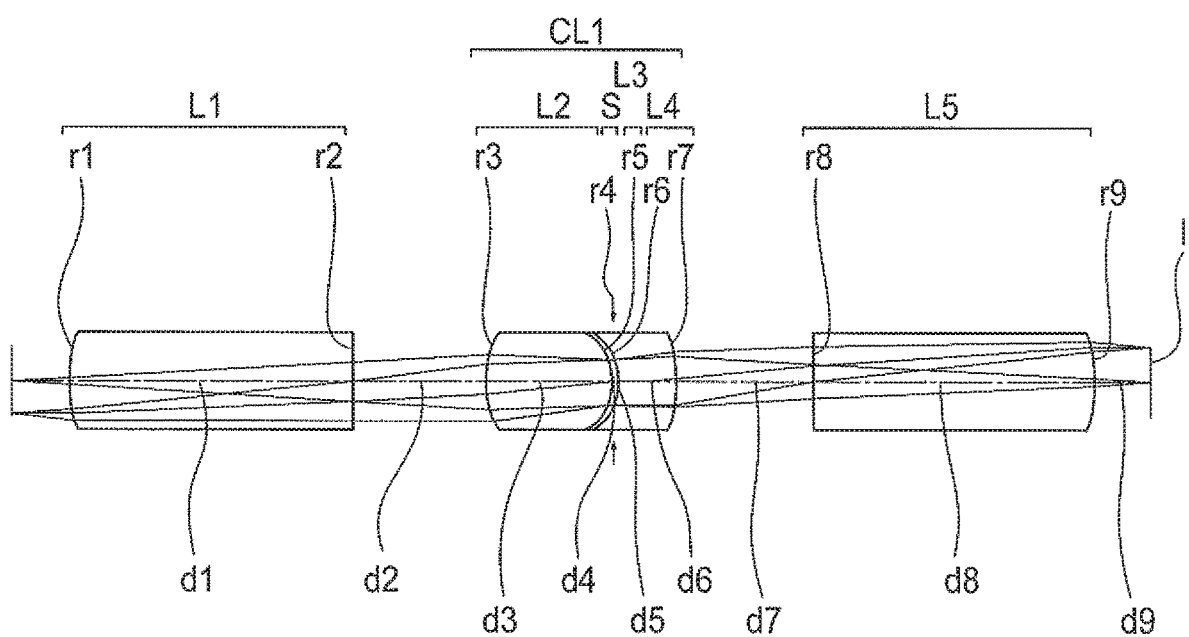
FIG. 9 is a lens cross-sectional view of a relay optical system of an example 5.
Figure 10:
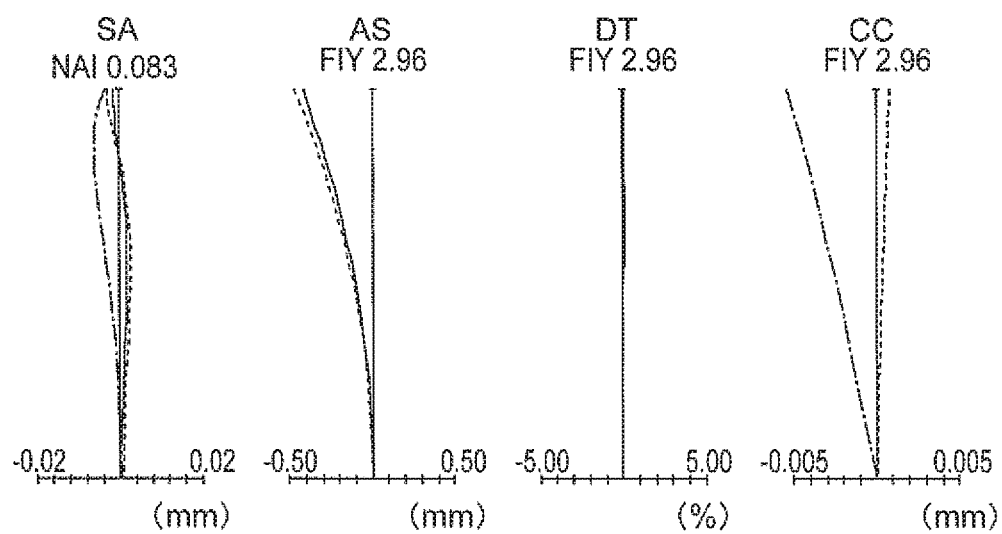
FIG. 10A, FIG. 10B, FIG. 10C, and FIG. 10D are aberration diagrams of the relay optical system of the example 5.
Figure 11:
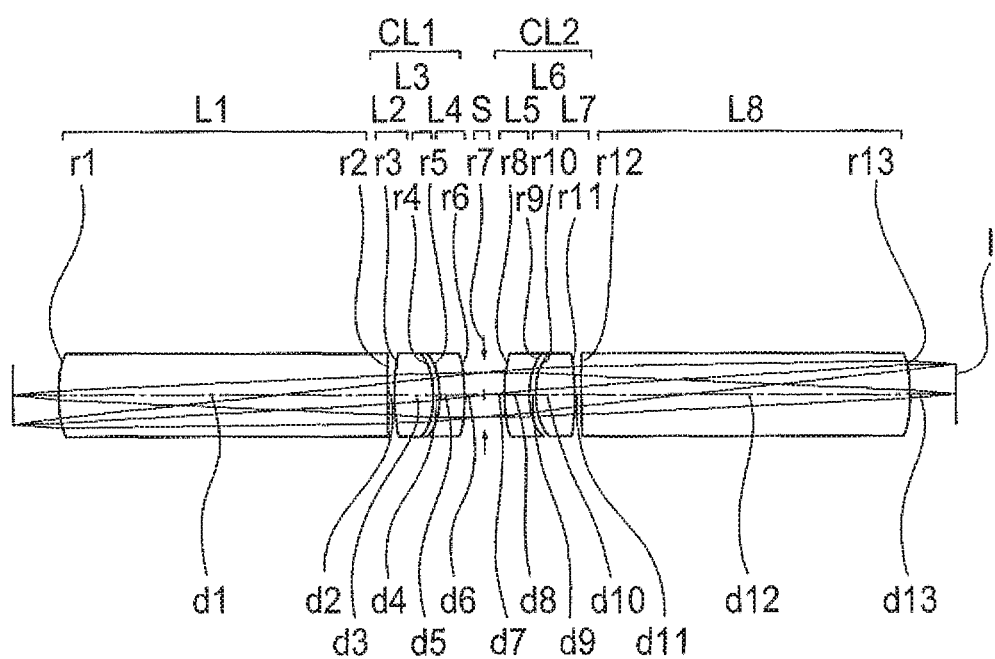
FIG. 11 is a lens cross-sectional view of a relay optical system of an example 6.
Figure 12:
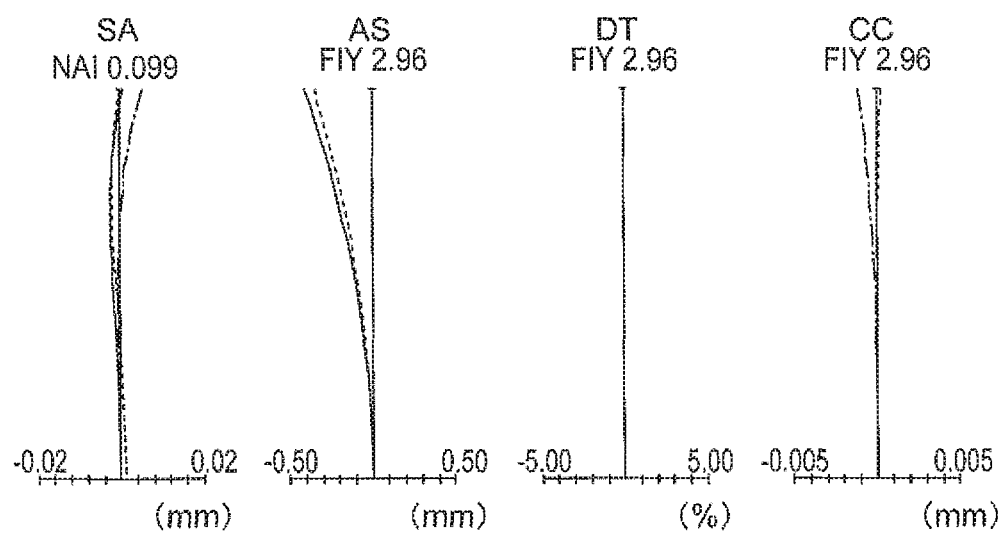
FIG. 12A, FIG. 12B, FIG. 12C, and FIG. 12D are aberration diagrams of the relay optical system of the example 6.
Figure 13:
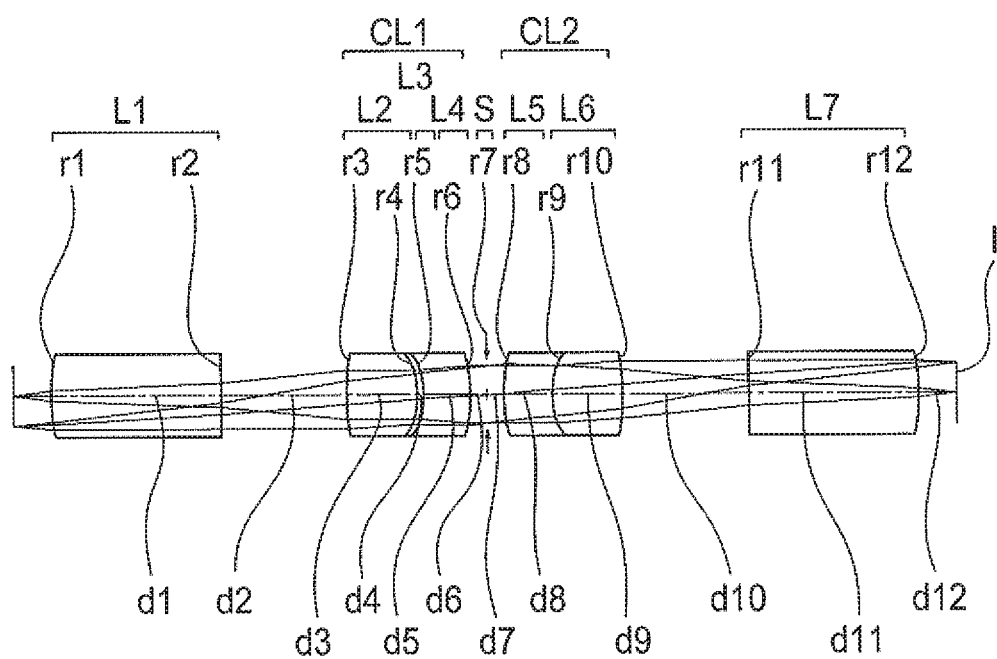
FIG. 13 is a lens cross-sectional view of a relay optical system of an example 7.
Figures 14A, 14B, 14C, 14D:
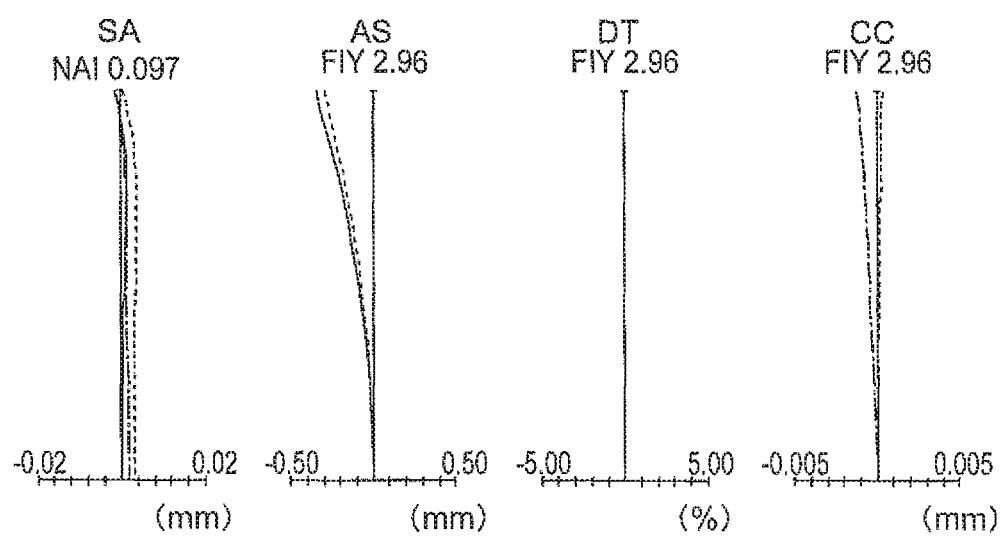
FIG. 14A, FIG. 14B, FIG. 14C, and FIG. 14D are aberration diagrams of the relay optical system of the example 7.
Figure 15:
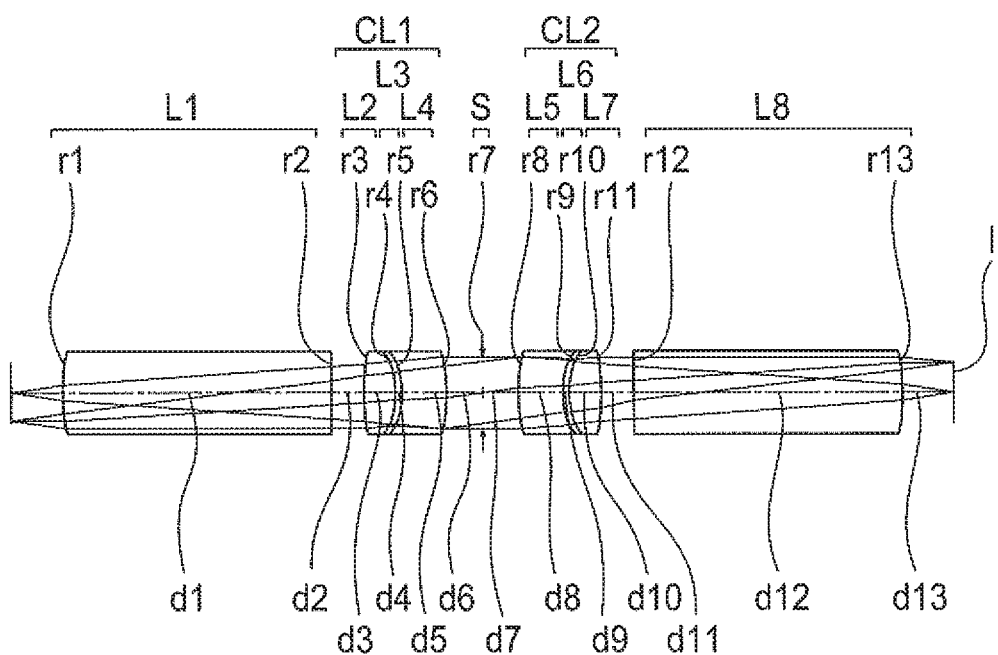
FIG. 15 is a lens cross-sectional view of a relay optical system of an example 8.
Figures 16A, 16B, 16C, 16D:
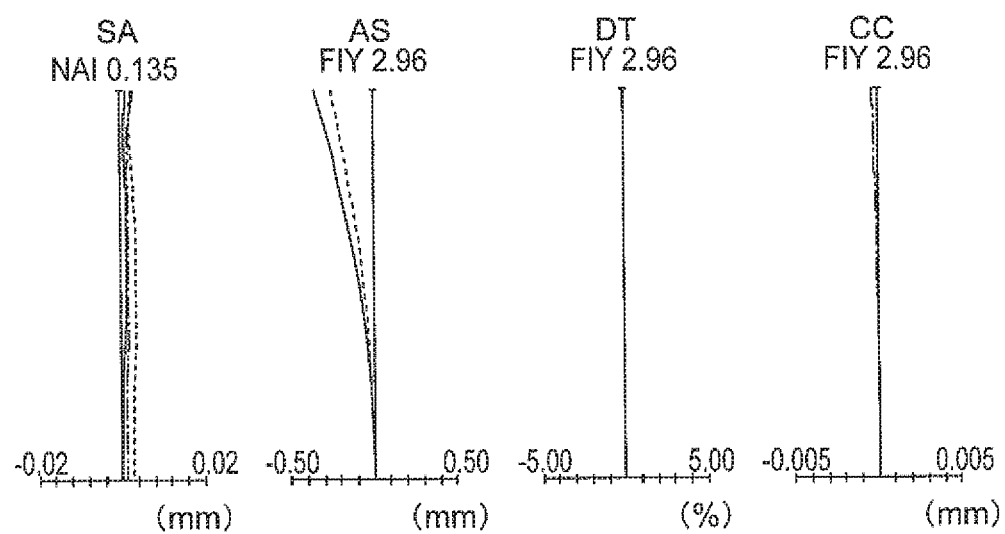
FIG. 16A, FIG. 16B, FIG. 16C, and FIG. 16D are aberration diagrams of the relay optical system of the example 8.
Figure 17:
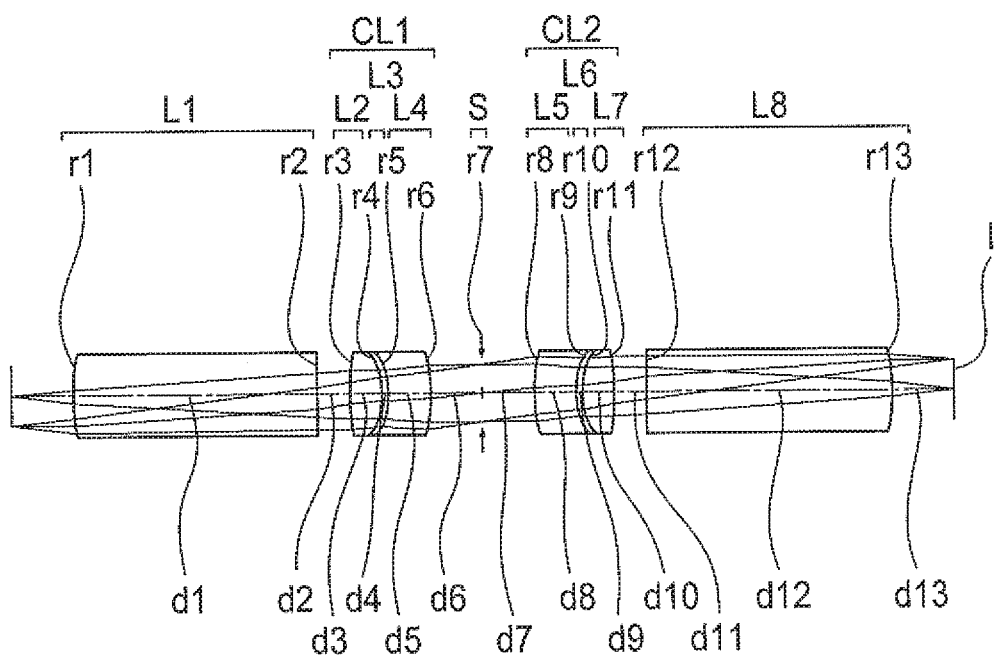
FIG. 17 is a lens cross-sectional view of a relay optical system of an example 9.
Figures 18A, 18B, 18C, 18D:
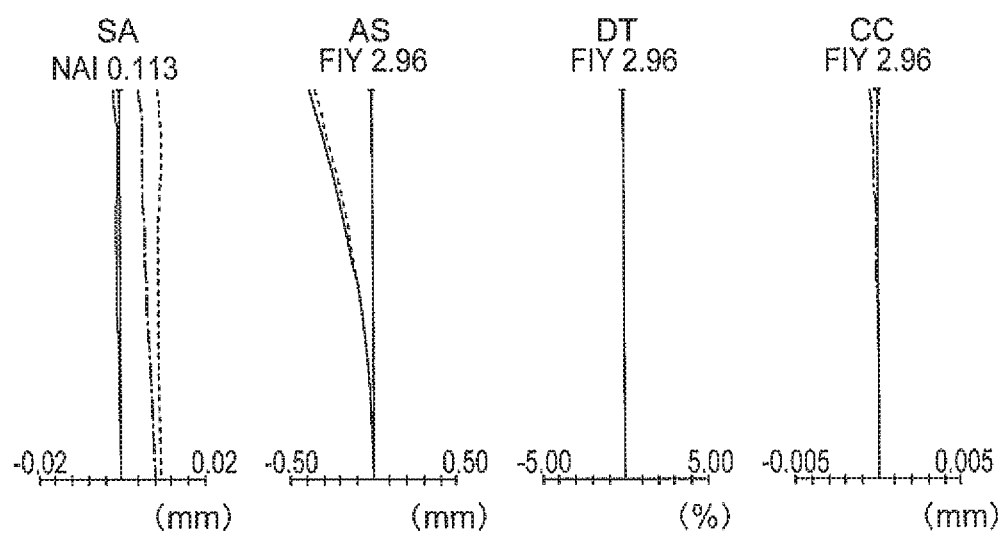
FIG. 18A, FIG. 18B, FIG. 18C, and FIG. 18D are aberration diagrams of the relay optical system of the example 9.

Reasons for and effects of adopting such arrangement for a relay optical system according to the present embodiment will be described below by using the accompanying diagrams. However, the present invention is not restricted to the relay optical system according to the present embodiment described below. Similar is true for an image relay unit, an optical system for rigid endoscope, and a rigid endoscope.

A relay optical system is used for relaying an image. The image relayed by a relay optical system is formed by an objective optical system. The objective optical system is disposed between an object and the relay optical system. A primary image of the object is formed by the objective optical system. The relay optical system relays the primary image, and forms an image (hereinafter, referred to as 'relay image'). An object side in the description below signifies a primary-image side, and an image side signifies a relay-image side. Moreover, an object plane signifies a plane at a position of the primary image, and an image plane signifies a plane at a position of the relay image.

The relay optical system of the present embodiment includes a cemented lens in which a first lens having a positive refractive power, a second lens having a positive refractive power, and a third lens having a negative refractive power are cemented, wherein the cemented lens is disposed in an optical path of the relay optical system, which is formed by an object-side optical path and an image-side optical path, and the first lens is a meniscus lens which is adjacent to the third lens, and a dispersion and a partial dispersion ratio differ for the first lens and the third lens, and in a rectangular coordinate system in which a horizontal axis is let to be $vd_{LA}$ and a vertical axis is let to be $\theta gF_{LA}$, when a straight line expressed by $\theta gF_{LA} = \alpha \times vd_{LA} + \beta_{LA}$ (where, $\alpha = -0.00163$) is set, $\theta gF_{LA}$ and $vd_{LA}$ of a medium of the first lens are included in an area determined by the following conditional expression (1) and conditional expression (2), and the following conditional expression (3) is satisfied:

$$0.67 \leq \beta_{LA} \qquad (1)$$

$$vd_{LA} < 50 \qquad (2)$$

$$-1.4 < mg < -0.6 \qquad (3)$$

where, $\theta gF_{LA}$ denotes a partial dispersion ratio $(ng_{LA} - nF_{LA})/(nF_{LA} - nC_{LA})$ of the medium of the first lens, $vd_{LA}$ denotes Abbe number $(nd_{LA} - 1)/(nF_{LA} - nC_{LA})$ for the medium of the first lens, and here $nd_{LA}$, $nC_{LA}$, $nF_{LA}$, and $ng_{LA}$ are refractive indices of the medium of the first lens for a d-line, a C-line, an F-line, and a g-line respectively, mg denotes a magnification of the relay optical system, the object-side optical path is an optical path positioned on an object side of a center of the relay optical system, and the image-side optical path is an optical path positioned on an image side of the center of the relay optical system.

In the relay optical system, it is necessary to relay the primary image without causing degradation of the primary image. In other words, it is necessary to make the relay image an image in which almost no degradation of the primary image has occurred. Therefore, it is important that no aberration is let to occur in the relay optical system as far as possible.

Aberrations that are susceptible to occur in a relay optical system are a chromatic aberration, a spherical aberration, and a curvature of field. Of these aberrations, it is preferable to correct favorably the chromatic aberration in particular.

A longitudinal chromatic aberration is an aberration in which a difference in a focal length for each color (a shift in focus) is indicated. Although the longitudinal chromatic aberration is an axial aberration, it also affects an off-axis imaging performance. When the longitudinal chromatic aberration occurs substantially, an imaging performance is degraded for each image height from the axial to the maximum image height.

As mentioned above, the relay optical system of the present embodiment includes the cemented lens in which the first lens, the second lens, and the third lens are cemented. The cemented lens is disposed in the optical path of the relay optical system.

It is possible to divide the optical path of the relay optical system into the object-side optical path and the image-side optical path, with the center of the relay optical system as a boundary, for example. The cemented lens is either to be disposed in at least one of the object-side optical path and the image-side optical path or to be disposed to be spread over both optical paths.

The first lens is a meniscus lens which is adjacent to the third lens. Moreover, each of the dispersion and the partial dispersion ratio differs for the first lens and the third lens. In such manner, the medium of the third lens has the dispersion and the partial dispersion ratio different from the dispersion and the partial dispersion ratio of the first lens. Therefore, it is possible to correct the chromatic aberration favorably by the first lens and the third lens.

In the relay optical system of the present embodiment, $\theta gF_{LA}$ and $vd_{LA}$ of the medium of the first lens are included in the area determined by conditional expression (1) and conditional expression (2).

By making such arrangement, the medium of the first lens becomes a medium having an abnormal dispersibility. The abnormal dispersibility is a dispersibility that differs from a dispersibility of a normal glass lens. In a lens in which a medium having the abnormal dispersibility is used (hereinafter, referred to as 'lens having abnormal dispersibility), it is possible to generate a large refractive power for light of a short wavelength. Therefore, in the first lens, by making appropriate the refractive power for the light of the short wavelength, it is possible to correct the longitudinal chromatic aberration effectively.

By making so as not to fall below a lower limit value of conditional expression (1), it is possible to correct appropriately a secondary spectrum in the longitudinal chromatic aberration, or in other words, an aberration for the g-line that remains when achromatized at the F-line and the C-line. By making so as not to exceed an upper limit value of conditional expression (2), it is possible to correct appropriately a first-order chromatic aberration in the longitudinal chromatic aberration.

Moreover, by using the lens having abnormal dispersibility, it is possible to correct the chromatic aberration of magnification and a high-order chromatic aberration. A wavelength interval difference in the spherical aberration and a wavelength interval difference in the coma are examples of the high-order chromatic aberration. The wavelength interval difference here refers to a difference in an aberration amount for two wavelengths. In a case of a plurality of wavelengths, the wavelength interval difference becomes a difference in an aberration amount for two arbitrary wavelengths.

Even when a light ray before being incident on the optical system is the same light ray, after passing through the optical system, the light ray is split for each wavelength due to dispersion. Consequently, a plurality of light rays reaches an image plane. Coordinates of a point of intersection of the light ray and the image plane differ for each wavelength. When coordinates of a light ray of a certain wavelength are let to be reference coordinates, there is a shift between the coordinates that are reference coordinates and coordinates of the point of intersection of a light ray of another wavelength. The wavelength interval difference is equivalent to that amount of shift.

It is possible to correct the chromatic aberration of magnification and the high-order chromatic aberration more favorably by improving symmetry of an optical system. Therefore, in a case of using the lens having abnormal dispersibility, it is preferable to improve the symmetry of an optical system. For improving the symmetry of the optical system, when a virtual plane is set at a center of the optical system, an arrangement of lenses, shape of lenses, or refractive power of lenses are to be symmetric on the object side and the image side.

Moreover, for relaying an image effectively, it is desirable to set a numerical aperture on the object side and a numerical aperture on the image side to be values that are close.

By making so as not to exceed an upper limit value of conditional expression (3), it is possible to prevent an image forming magnification from becoming excessively large. As a result, it is possible to suppress an occurrence of the longitudinal chromatic aberration, an occurrence of the coma, and an occurrence of the chromatic aberration of magnification. In a case in which it is possible to improve the symmetry of the optical system, it is possible to suppress further, particularly the occurrence of the coma and the occurrence of the chromatic aberration of magnification.

By making so as not to fall below a lower limit value of conditional expression (3), it is possible to prevent the numerical aperture on the object side from becoming excessively small. As a result, it is possible to suppress the occurrence of the coma and the occurrence of the chromatic aberration of magnification. In a case in which it is possible to improve the symmetry of the optical system, it is possible to suppress further particularly the occurrence of the coma and the occurrence of the chromatic aberration of magnification.

It is preferable that the following conditional expression (1') be satisfied instead of conditional expression (1).

$$0.71 \leq \beta_{LA} < 0.9 \tag{1'}$$

It is preferable that the following conditional expression (2') be satisfied instead of conditional expression (2).

$$3 < vd_{LA} < 50 \tag{2'}$$

It is preferable that the following conditional expression (3') be satisfied instead of conditional expression (3)

$$-1.2 < mg < -0.8 \tag{3'}$$

By making so as not to exceed an upper limit value of conditional expression (1'), it is possible to prevent a correction of the secondary spectrum in the longitudinal chromatic aberration from becoming excessive. By making so as not to fall below a lower limit value of conditional expression (2'), it is possible to prevent a correction of the first-order chromatic aberration in the longitudinal chromatic aberration from becoming excessive.

In the relay optical system of the present embodiment, a medium not having the abnormal dispersibility may be used as the medium of the third lens.

As mentioned above, the medium of the first lens has the abnormal dispersibility. Whereas, the medium of the third lens has the dispersion and partial dispersion ratio differing from that of the medium of the first lens. Therefore, a medium not having the abnormal dispersibility, or in other words, a medium of normal dispersion is to be used as the medium of the third lens.

A medium of the normal dispersion is a medium for which, in a rectangular coordinate system in which a horizontal axis is let to be $vd_L$ and a vertical axis is let to be $\theta gF_L$, when a straight line expressed by $\theta gF_L = \alpha \times vd_L + \beta_L$ (where, $\alpha = -0.00163$) is set, $\theta gF_L$ of the medium of the lens is not included in an area determined by the following conditional expression (A).

$$0.67 \leq \beta_L \quad (A)$$

where, $vd_L$ denotes Abbe number $(nd_L-1)/(nF_L-nC_L)$ for the medium of the lens, and here $nd_L$, $nC_L$, $nF_L$, and $ng_L$ are refractive indices of the medium of the lens for the d-line, the C-line, the F-line, and the g-line respectively.

In this case, when the third lens and the first lens are let to be adjacent, one lens in which the medium having the abnormal dispersibility and the medium having the normal dispersibility are combined (hereinafter, referred to as 'compound lens') is formed. The compound lens has two media. When the two media are deemed as one medium, the medium of the compound lens has the abnormal dispersibility virtually. Therefore, it is possible to correct the chromatic aberration favorably by the compound lens and the second lens.

Moreover, for correcting the chromatic aberration favorably, a difference in Abbe number for the media of the two lenses is to be made large and a difference in the partial dispersion ratio is to be made small. When the third lens and the first lens are let to be a compound lens, a degree of freedom for realizing a favorable difference in Abbe number and a favorable partial dispersion ratio increases. Consequently, it is possible to carry out ideally a reduction in the first-order chromatic aberration in the longitudinal chromatic aberration and a reduction in the secondary spectrum in the longitudinal chromatic aberration.

In such manner, in the relay optical system of the present embodiment, by forming the compound lens by the first lens having the abnormal dispersibility and the third lens having the dispersion and partial dispersion ratio different from that of the first lens as well as by combining the compound lens and the second lens, the chromatic aberration is corrected favorably.

In assembling the optical system, lenses are housed in holding frames one after another. Generally, even though the chromatic aberration of the optical system has been corrected favorably in design, when lenses are decentered due to a manufacturing error, in a state of the optical system assembled initially, it may be difficult to make a state in which the chromatic aberration is corrected favorably. Particularly, the chromatic aberration of magnification and the high-order chromatic aberration become large due to decentering of lenses.

As mentioned above, since the medium of the first lens has the abnormal dispersibility, by combining with the second lens and the third lens, it is possible to correct the chromatic aberration favorably. At this time, when each of the first lens, the second lens, and the third lens are disposed to be separated apart, decentering is susceptible to occur between these lenses.

To prevent an occurrence of the decentering, decentering adjustment is carried out in a manufacturing process, and an arrangement is made such that an aberration-correction state is maintained appropriately. When the first lens and the second lens are disposed to be separated apart, an adjustment work in the decentering adjustment becomes complicated. Similar is a case in which the first lens and the third lens are disposed to be separated apart and a case in which the second lens and the third lens are disposed to be separated apart.

Whereas, by cementing the first lens, the second lens, and the third lens, the decentering is hard to occur between these lenses. As a result, the necessity of the decentering adjustment is reduced, and it is possible to carry out a correction of the high-order chromatic aberration and a correction of the chromatic aberration of magnification favorably while simplifying the manufacturing process.

Particularly, it is preferable to set the partial dispersion ratio of the second lens and the partial dispersion ratio of the third lens to differ from the partial dispersion ratio of the first lens. By making such arrangement, it is possible to carry out the correction of the high-order chromatic aberration and the correction of the chromatic aberration of magnification more favorably.

However, when the decentering occurs between these lenses, it becomes difficult to achieve a favorable correction effect. By cementing the first lens, the second lens, and the third lens, it is possible to make small the decentering between these lenses. As a result, it is possible to carryout the correction of the high-order chromatic aberration and the correction of the chromatic aberration of magnification more favorably.

For cementing, a method of fixing lenses by a cementing material, a method of fixing lenses by bringing in direct contact (optical contact) without using a cementing material, or a method of fixing lenses by curing a resin is to be used. The method of fixing two lenses by curing a resin will be described later.

The combination of lenses to be cemented may be any one of only glass lenses, a glass lens and a resin lens, and only resin lenses.

There is a case in which one of the lenses to be cemented is a resin lens which is thin in thickness. In this case, by using the method of curing the resin that will be described later, it is possible to fix the thin resin lens and the other lens. In this method, a cementing material may not be interposed between the two lenses. A cementing material may be interposed between the two lenses, and the thin resin lens and the other lens may be fixed.

In the relay optical system of the present embodiment, it is preferable that the first lens be positioned between the second lens and the third lens. Moreover, in the relay optical system of the present embodiment, it is preferable that the third lens be positioned between the second lens and the first lens.

In a relay optical system, an angle of refraction of a light ray varies substantially at each lens surface. In other words, within a relay optical system, a direction in which light advances varies substantially. Consequently an aberration is susceptible to occur. For suppressing an occurrence of aberration, it is desirable to make an arrangement such that light is refracted gradually within the relay optical system.

The third lens has a negative refractive power. In this case, since a divergence effect occurs in the third lens, the angle of refraction of a light ray is susceptible to vary substantially. Therefore, the cemented lens is arranged such that the third lens is positioned at a center of the relay optical system. By making such arrangement, a light ray passing through the cemented lens is refracted gradually. As a result, it is possible to suppress an occurrence of aberration in the cemented lens.

More specifically, the cemented lens includes in order from the object side, either the second lens, the first lens, and the third lens, or the second lens, the third lens, and the first lens. By making such arrangement, a light ray passing through the cemented lens is refracted gradually. As a result, it is possible to suppress the occurrence of aberration in the cemented lens.

At this time, it is possible to let the second lens to be a lens having a biconvex shape, the first lens to be a meniscus lens having a concave surface directed toward the object side, and the third lens to be a meniscus lens having a concave surface directed toward the object side.

In a case of disposing the cemented lens each, in the object-side optical path and the image-side optical path, an arrangement is to be made such that the cemented lens in the object-side optical path has the abovementioned arrangement.

In the relay optical system of the present embodiment, it is preferable that the first lens be a resin lens.

By making such arrangement, it is possible to make small the decentering which occurs between the two lenses. Moreover, it is possible to make the lenses further thinner.

In a case in which the first lens is a resin lens, it is possible to use the method of fixing two lenses by curing a resin. In this method, the first lens is cured upon bringing in close contact with a surface of another lens. The description will be made below by using the first lens and the second lens.

In curing upon bringing in close contact, a liquid resin such as an ultraviolet cure resin is to be used. As a lens material of the first lens, a material such as an ultraviolet cure resin is available. A desired amount of the ultraviolet cure resin is to be discharged on to a refractive surface of the second lens. Accordingly, the ultraviolet cure resin is in a state of making a contact with the refractive surface of the second lens. Of surfaces of the ultraviolet cure resin, a surface in contact with the refracting surface of the second lens is one refracting surface of the first lens.

A mold is disposed at a position facing the second lens, sandwiching the ultraviolet cure resin. The mold is pressed against the ultraviolet cure resin. The ultraviolet cure resin assumes a state of being sandwiched between the mold and the second lens. In this state, ultraviolet rays are irradiated from the second lens side. Accordingly, the ultraviolet cure resin is cured.

The mold has a molding surface. The molding surface is a surface in contact with the ultraviolet cure resin. A shape of the molded surface is same as a shape of the other refracting surface of the first lens. Of the surfaces of the ultraviolet cure resin, a surface in contact with the molded surface is the other refracting surface of the first lens.

In such manner, in curing up on bringing in close contact, the one refracting surface of the first lens is formed by the refracting surface of the second lens, and the other refracting surface of the first lens is formed by the molded surface of the mold.

A material of the first lens is not restricted to the ultraviolet cure resin. The method of curing is also not restricted to a method in which the ultraviolet rays are irradiated.

By curing upon bringing in close contact, it is possible to make small a surface-shape error and a decentering error. Furthermore, it is possible to make the lens thin.

In the relay optical system of the present embodiment, it is preferable that the following conditional expression (4) be satisfied:

$$0<|(R1-R2)/(R1+R2)|<3 \quad (4)$$

where,

R1 denotes a radius of curvature of an object side of the first lens, and

R2 denotes a radius of curvature of an image side of the first lens.

As mentioned above, the medium of the first lens has the abnormal dispersibility. Therefore, by making appropriate the refractive power for the light of the short wavelength, it is possible to correct the longitudinal chromatic aberration favorably. For this, it is significant to optimize the radius of curvature of the first lens.

By making so as not to exceed an upper limit value of conditional expression (4), it is possible to prevent the refractive power of the first lens from becoming excessively large. As a result, it is possible to prevent the chromatic aberration on the short wavelength side from being corrected excessively.

By making so as not to fall below a lower limit value of conditional expression (4), it is possible to secure appropriately the refractive power of the first lens. As a result, it is possible to prevent the chromatic aberration on the short wavelength side from being corrected inadequately.

It is more preferable that the following conditional expression (4') be satisfied instead of conditional expression (4).

$$0<|(R1-R2)/(R1+R2)|<2 \quad (4')$$

It is even more preferable that the following conditional expression (4") be satisfied instead of conditional expression (4).

$$0<|(R1-R2)/(R1+R2)|<0.6 \quad (4")$$

In the relay optical system of the present embodiment, it is preferable that the following conditional expressions (5) and (6) be satisfied:

$$1.4<nd_{LB}<1.6 \quad (5)$$

$$50<vd_{LB}<100 \quad (6)$$

where, $nd_{LB}$ denotes a refractive index of a medium of the second lens for the d-line, and $vd_{LB}$ denotes Abbe number $(nd_{LB}-1)/(nF_{LB}-nC_{LB})$ for the medium of the second lens, and here $nd_{LB}$, $nC_{LB}$, $nF_{LB}$, and $ng_{LB}$ are refractive indices of the medium of the second lens for the d-line, the C-line, the F-line, and the g-line.

By making such arrangement, it is possible to suppress the chromatic aberration in the second lens. Consequently, by the combination of the first lens and the third lens, it is possible to carry out a correction of the chromatic aberration more favorably.

It is more preferable that the following conditional expression (5') be satisfied instead of conditional expression (5).

$$1.4<nd_{LB}<1.55 \quad (5')$$

It is more preferable that the following conditional expression (6') be satisfied instead of conditional expression (6).

$$60<vd_{LB}<100 \quad (6)$$

In the relay optical system of the present embodiment, it is preferable that the cemented lens be disposed in at least one of the object-side optical path and the image-side optical path.

By making such arrangement, at least one cemented lens is disposed in the optical path of the relay optical system. As mentioned above, by using the cemented lens, it is possible to correct the chromatic aberration favorably. Therefore, it is possible to realize a relay optical system in which the chromatic aberration is small.

In the relay optical system of the present embodiment, it is preferable that the cemented lens be disposed in each of the object-side optical path and the image-side optical path.

By making such arrangement, a plurality of cemented lenses is disposed in the optical path. As mentioned above, by using the cemented lens, it is possible to correct the chromatic aberration favorably. Therefore, it is possible to realize a relay optical system in which the chromatic aberration is further smaller.

Moreover, in a case in which the number of cemented lenses is one, the required refractive power is shared by three lenses. Whereas, in a case in which the number of cemented lenses is in plurality, it is possible to divide the required refractive power among six or more than six lenses.

When it is possible to divide the required refractive power among six or more than six lenses, it is possible to suppress further the occurrence of aberration in each lens. As a result, it is possible to reduce further an amount of occurrence of the chromatic aberration in the relay optical system.

Moreover, it is possible to make small an amount of occurrence of an aberration with respect to the predetermined decentering amount. Even when there is the decentering due to a manufacturing error, it is possible to make the adjustment work in the decentering adjustment easy. Therefore, it is possible to suppress the degradation of imaging performance while simplifying the manufacturing process.

The cemented lens is disposed in both the object-side optical path and the image-side optical path. Therefore, it is possible to dispose the cemented lenses to be symmetrical in the object-side optical path and the image-side optical path. By making such arrangement, it is possible to realize a relay optical system in which, in addition to the chromatic aberration, the coma and a distortion are corrected favorably.

The number of cemented lenses to be disposed in the object-side optical path is not restricted to one. Similar is true for the image-side optical path. Moreover, the number of cemented lenses may be same or may be different in each the object-side optical path and the image-side optical path.

For instance, in an optical system for rigid endoscope, a plurality of relay optical systems is used. An overall length of a rigid endoscope, or in other words, an overall length of the optical system for rigid endoscope is set to a length appropriate for a target of use or a method of use. The overall length of the optical system for rigid endoscope is almost determined by the number of relay optical systems and an overall length of relay optical system. In a case of realizing the desired overall length by adjusting the number of relay optical systems, it is possible to adjust the overall length minutely when the length of the relay optical system is short. Therefore, it is preferable that the overall length of the relay optical system be short.

For such reason, in the relay optical system of the present embodiment, it is preferable that the number of cemented lenses to be disposed in the optical path of the relay optical system be one or two.

By making such arrangement, it is possible to realize a relay optical system having a short overall length, in which the chromatic aberration is corrected favorably. As a result, it is possible to realize easily the optical system for rigid endoscope having the desired overall length.

It is preferable that the relay optical system of the present embodiment include at least one aspheric surface.

When the numerical aperture of the optical system is made large, the farther the position through which light passes, in a marginal area from an optical axis, the chromatic aberration is corrected excessively. Therefore, an arrangement is made such that the relay optical system includes at least one aspheric surface. By making such arrangement, it is possible to make the refractive power appropriate throughout the entire marginal area. As a result, even in a relay optical system with a large numerical aperture, it is possible to carry out the correction of the chromatic aberration in the marginal area favorably.

As mentioned above, the medium of the first lens has the abnormal dispersibility. Therefore, by using the first lens, it is possible to correct the longitudinal chromatic aberration favorably. However, in the first lens, it is preferable to make appropriate the refractive power for the light of the short wavelength according to a size of the numerical aperture of the optical system.

It is possible to make appropriate the refractive power for the light of the short wavelength by using an aspheric surface. Therefore, it is preferable to provide the aspheric surface to the first lens. By making such arrangement, even in a relay optical system with a large numerical aperture, it is possible to carry out the correction of the chromatic aberration in the marginal area more favorably.

The aspheric surface may be provided to a surface on one side of the lens or to surfaces on both sides of the lens. Moreover, the number of lenses to be provided with the aspheric surface is not restricted to one.

It is preferable that the relay optical system of the present invention include an object-side lens which is disposed in the object-side optical path and an image-side lens which is disposed in the image-side optical path, and the object-side lens have a positive refractive power, and be disposed such that a convex surface is directed toward the object side, and the image-side lens have a positive refractive power, and be disposed such that a convex surface is directed toward the image side, and the cemented lens be disposed between the object-side lens and the image-side lens.

As mentioned above, in the relay optical system, it is necessary to relay the primary image without being degraded. For this, it becomes significant to suppress a loss of quantity of light in a periphery of a relay image. Moreover, it becomes significant to suppress the occurrence of aberration in the relay optical system.

The relay optical system of the present embodiment includes the object-side lens which is disposed in the object-side optical path and the image-side lens which is disposed in the image-side optical path. Moreover, the cemented lens is disposed between the object-side lens and the image side lens. Consequently, the object-side lens is disposed nearest to the object and the image-side lens is disposed nearest to the image.

Here, the object-side lens has a positive refractive power, and is disposed such that the convex surface is directed toward the object side. Consequently, it is possible to let the relay optical system to be an optical system which is telecentric on the object side. Moreover, the image-side lens has a positive refractive power and is disposed such that the convex surface is directed toward the image side. Consequently, it is possible to let the relay optical system to be an optical system which is telecentric on the image side.

In such manner, in the relay optical system of the present embodiment, it is possible to maintain a favorable telecentricity on both the object side and the image side. Consequently, it is possible to suppress the loss of quantity of light in the periphery of the relay image. As a result, it is possible to relay the primary image without being degraded.

Moreover, by providing such arrangement, it is possible to use the cemented lens disposed between the object-side lens and the image-side lens for correcting the chromatic aberration in particular. As a result, it is possible to carry out the correction of the chromatic aberration favorably.

As mentioned above, in the relay optical system of the present embodiment, the optical system being the telecentric optical system on both the object side and the image side, a principal light ray is parallel to the optical axis on both the object side and the image side. In this state, by determining a shape and thickness etc. of a lens such that a light ray passing through the cemented lens is refracted gradually without being deviated substantially from the state of being parallel to the optical axis, it is possible to suppress an occurrence of aberration in the cemented lens, and to suppress an occurrence of aberration in the relay optical system. As a result, it is possible to relay the primary image without being degraded.

In the relay optical system of the present embodiment, it is preferable that a lens surface positioned nearest to the image in the object-side optical path be a surface which is convex toward the image side, and a lens surface positioned nearest to the object in the image-side optical path be a surface which is convex toward the object side.

In a relay optical system, a light-ray height becomes high near a center of the relay optical system. Consequently, the spherical aberration and the coma are susceptible to occur in a lens disposed at a position separated away from the primary-image position and a lens disposed at a position separated away from the relay-image position. Therefore, when the abovementioned arrangement is made, it becomes a state in which two convex surfaces are face-to-face at the center of the lenses. As a result, it is possible to suppress an occurrence of the spherical aberration and the occurrence of the coma.

In the relay optical system of the present embodiment, it is preferable that the cemented lens be disposed symmetrically near the center of the relay optical system.

By making such arrangement, two convex surfaces are face-to-face at the center of the relay optical system. As a result, it is possible to suppress the occurrence of the spherical aberration and the occurrence of the coma.

It is preferable that the lens positioned nearest to the image in the object-side optical path and the lens positioned nearest to the object in the image-side optical path be the first lens. Or, instead of the first lens, the third lens may be positioned.

It is preferable that the relay optical system of the present embodiment include a cemented lens, and the cemented lens include at least the first lens, and the following conditional expression (7) be satisfied:

$$0.2 < (OBH+IH)/\Phi_{ce} < 1.8 \tag{7}$$

where, $\Phi_{ce}$ denotes a light-ray effective diameter of the cemented lens,

OBH denotes the maximum object height, and

IH denotes the maximum image height.

In relay optical systems, there are a relay optical system in which an image height of the primary image is high, a relay optical system in which an image height of the relay image is high, and a relay optical system in which both the image height of the primary image and the image height of the relay image are high. In such relay optical systems in which the image height is high, a height of a light ray that passes through the relay optical system also becomes high. As a result, an angle of incidence on a lens positioned at a center of the relay optical system tends to becomes large.

In the relay optical system of the present embodiment, the first lens, or in other words, the lens having abnormal dispersibility is disposed near the center of the relay optical system. When an angle of incidence on the lens having abnormal dispersibility becomes large, with the image height becoming high, it becomes difficult to carry out adequately the correction of the chromatic aberration in an optical axial direction.

Therefore, by satisfying conditional expression (7), it is possible to correct favorably the chromatic aberration in the optical axial direction. The light-ray effective diameter is a diameter in which the maximum light-ray height among the light-ray height of light rays passing through the cemented lens is doubled.

By making so as not to exceed an upper limit value of conditional expression (7), even in a relay optical system in which the image height is high, it is possible to prevent the correction of the chromatic aberration in the optical axial direction from becoming inadequate. By making so as not to fall below a lower limit value of conditional expression (7), it is possible to suppress a size in a radial direction of the relay optical system from becoming large while maintaining high the image height of the primary image and the image height of the relay image.

It is more preferable that the following conditional expression (7') be satisfied instead of conditional expression (7).

$$0.4 < (OBH+IH)/\Phi_{ce} < 1.5 \tag{7'}$$

It is even more preferable that the following conditional expression (7") be satisfied instead of conditional expression (7).

$$0.6 < (OBH+IH)/\Phi_{ce} < 1.2 \tag{7"}$$

In the relay optical system of the present embodiment, it is preferable that the following conditional expressions (8) and (9) be satisfied:

$$0.05 < NA < 0.3 \tag{8}$$

$$50 \text{ mm} < |FL| \tag{9}$$

where,

NA denotes a numerical aperture of the relay optical system, and

FL denotes a focal length of the relay optical system.

By satisfying conditional expressions (8) and (9), it is possible to realize a relay optical system having a short overall length, and which enables to form a relay image with high-resolution.

An image relay unit of the present embodiment includes a plurality of relay optical systems, wherein at least one relay optical system of the plurality of relay optical systems is the relay optical system of the present embodiment.

As mentioned above, in the relay optical system of the present embodiment, the chromatic aberration is corrected favorably. Therefore, by using at least one relay optical system of the present embodiment in the image relay unit, it is possible to realize an image relay unit in which the chromatic aberration is small. By using the plurality of relay optical systems of the present embodiment, it is possible to realize an image relay unit in which the chromatic aberration is further smaller.

For forming a relay image with high resolution, it is desirable to make large the numerical aperture of the relay optical system. However, when the numerical aperture of the relay optical system is made large, the chromatic aberration is susceptible to occur.

Moreover, it is possible to use the image relay unit in an optical system for rigid endoscope. As mentioned above, in a case of making appropriate the overall length of the optical system for rigid endoscope by adjusting the number of relay optical systems, it is preferable that the overall length of the relay optical system be short. When the overall length of the relay optical system is made short, the numerical aperture becomes large. Even in this case, the chromatic aberration is susceptible to occur.

In the relay optical system of the present embodiment, the chromatic aberration is corrected favorably. Therefore, even when the numerical aperture is made large, it is possible to suppress an increase in the chromatic aberration. Therefore, by using the relay optical system of the present embodiment in the image relay unit, it is possible to realize an image relay unit which has a large numerical aperture and in which the chromatic aberration is corrected favorably.

An optical system for rigid endoscope of the present embodiment includes an objective optical system and an image relay unit which is disposed on the image side of the objective optical system, wherein the image relay unit is the image relay unit of the present embodiment.

By using the image relay unit of the present embodiment, it is possible to realize an optical system for rigid endoscope in which the chromatic aberration is corrected favorably.

It is preferable that the optical system for endoscope of the present embodiment include an eyepiece optical system which is disposed on the image side of the image relay unit.

By making such arrangement, it is possible to observe an optical image in which the chromatic aberration is corrected favorably.

A rigid endoscope of the present embodiment includes the optical system for rigid endoscope and an image pickup element which captures an image formed by the image relay unit.

When the optical system for rigid endoscope of the present embodiment is used, an optical image is formed by the image relay unit of the present embodiment. The chromatic aberration is corrected favorably in this optical image. Therefore, by capturing this optical image by the image pickup element, it is possible to acquire an image with a small chromatic aberration.

It is preferable that the rigid endoscope of the present embodiment include an illuminating unit for illuminating the object to be observed.

By making such arrangement, it is possible to carry out an observation of an optical image with a small chromatic aberration and an acquisition of an image with the small chromatic aberration.

Examples of the relay optical system, the optical system for rigid endoscope, and the rigid endoscope will be described below in detail by referring to the accompanying diagrams. However, the present invention is not restricted to the examples described below.

Examples of the relay optical system will be described below. FIG. 1, FIG. 3, FIG. 5, FIG. 7, FIG. 9, FIG. 11, FIG. 13, FIG. 15, and FIG. 17 are lens cross-sectional views of relay optical systems of the examples.

Aberration diagrams of the examples will be described below.

FIG. 2A, FIG. 4A, FIG. 6A, FIG. 8A, FIG. 10A, FIG. 12A, FIG. 14A, FIG. 16A, and FIG. 18A show a spherical aberration (SA).

FIG. 2B, FIG. 4B, FIG. 6B, FIG. 8B, FIG. 10B, FIG. 12B, FIG. 14B, FIG. 16B, and FIG. 18B show an astigmatism (AS). FIG. 2C, FIG. 4C, FIG. 6C, FIG. 8C, FIG. 10C, FIG. 12C, FIG. 14C, FIG. 16C, and FIG. 18C show a distortion (DT). FIG. 2D, FIG. 4D, FIG. 6D, FIG. 8D, FIG. 10D, FIG. 12D, FIG. 14D, FIG. 16D, and FIG. 18D show a chromatic aberration of magnification (CC).

In each example, an aperture stop S is disposed in the relay optical system. However, the aperture stop S may not have been disposed in the relay optical system provided that it is possible to determine a light-beam diameter even without using the aperture stop S.

A relay optical system of an example 1 includes in order from an object side, a planoconvex positive lens L1, a cemented lens CL1 having a positive refractive power, a cemented lens CL2 having a positive refractive power, and a planoconvex positive lens L8. The aperture stop S is disposed between the cemented lens CL1 and the cemented lens CL2.

The cemented lens CL1 includes a biconvex positive lens L2, a positive meniscus lens L3 having a convex surface directed toward an image side, and a negative meniscus lens L4 having a convex surface directed toward the image side. The cemented lens CL2 includes a negative meniscus lens L5 having a convex surface directed toward the object side, a positive meniscus lens L6 having a convex surface directed toward the object side, and a biconvex positive lens L7.

The positive meniscus lens L3 is the first lens and the positive meniscus lens L6 is the first lens. The biconvex positive lens L2 is the second lens and the biconvex positive lens L7 is the second lens. The negative meniscus lens L4 is the third lens and the negative meniscus lens L5 is the third lens.

In the relay optical system of the example 1, the planoconvex positive lens L1 and the planoconvex positive lens L8 are symmetrical with respect to the aperture stop S. Moreover, the cemented lens CL1 and the cemented lens CL2 are symmetrical with respect to the aperture stop S. In the relay optical system of the example 1, a symmetry plane exists at a position of the aperture stop S.

An aspheric surface is provided to a total of two surfaces which are an image-side surface of the positive meniscus lens L3 and an object-side surface of the positive meniscus lens L6.

A relay optical system of an example 2 includes in order from an object side, a planoconvex positive lens L1, a cemented lens CL1 having a positive refractive power, a cemented lens CL2 having a positive refractive power, and a planoconvex positive lens L8. An aperture stop S is disposed between the cemented lens CL1 and the cemented lens CL2.

The cemented lens CL1 includes a biconvex positive lens L2, a positive meniscus lens L3 having a convex surface directed toward an image side, and a negative meniscus lens L4 having a convex surface directed toward the image side.

The cemented lens CL2 includes a negative meniscus lens L5 having a convex surface directed toward the object side, a positive meniscus lens L6 having a convex surface directed toward the object side, and a biconvex positive lens L7.

The positive meniscus lens L3 is the first lens and the positive meniscus lens L6 is the first lens. The biconvex positive lens L2 is the second lens and the biconvex positive lens L7 is the second lens. The negative meniscus lens L4 is the third lens and the negative meniscus lens L5 is the third lens.

In the relay optical system of the example 2, the planoconvex positive lens L1 and the planoconvex positive lens L8 are symmetrical with respect to the aperture stop S. Moreover, the cemented lens CL1 and the cemented lens CL2 are symmetrical with respect to the aperture stop S. In the relay optical system of the example 2, a symmetry plane exists at a position of the aperture stop S.

An aspheric surface is provided to a total of two surfaces which are an image-side surface of the positive meniscus lens L3 and an object-side surface of the positive meniscus lens L6.

A relay optical system of an example 3 includes in order from an object side, a biconvex positive lens L1, a cemented lens CL1 having a positive refractive power, a cemented lens CL2 having a positive refractive power, and a biconvex positive lens L8. An aperture stop S is disposed between the cemented lens CL1 and the cemented lens CL2.

The cemented lens CL1 includes a biconvex positive lens L2, a negative meniscus lens L3 having a convex surface directed toward an image side, and a positive meniscus lens L4 having a convex surface directed toward the image side.

The cemented lens CL2 includes a positive meniscus lens L5 having a convex surface directed toward the object side, a negative meniscus lens L6 having a convex surface directed toward the object side, and a biconvex positive lens L7.

The positive meniscus lens L4 is the first lens and the positive meniscus lens L5 is the first lens. The biconvex positive lens L2 is the second lens and the biconvex positive lens L7 is the second lens. The negative meniscus lens L3 is the third lens and the negative meniscus lens L6 is the third lens.

In the relay optical system of the example 3, the biconvex positive lens L1 and the biconvex positive lens L8 are symmetrical with respect to the aperture stop S. Moreover, the cemented lens CL1 and the cemented lens CL2 are symmetrical with respect to the aperture stop S. In the relay optical system of the example 3, a symmetry plane exists at a position of the aperture stop S.

An aspheric surface is provided to a total of two surfaces which are an image-side surface of the positive meniscus lens L4 and an object-side surface of the positive meniscus lens L5.

A relay optical system of an example 4 includes in order from an object side, a planoconvex positive lens L1, a cemented lens CL1 having a positive refractive power, a cemented lens CL2 having a positive refractive power, and a planoconvex positive lens L8. An aperture stop S is disposed between the cemented lens CL1 and the cemented lens CL2.

The cemented lens CL1 includes a biconvex positive lens L2, a positive meniscus lens L3 having a convex surface directed toward an image side, and a negative meniscus lens L4 having a convex surface directed toward the image side.

The cemented lens CL2 includes a negative meniscus lens L5 having a convex surface directed toward the object side, a positive meniscus lens L6 having a convex surface directed toward the object side, and a biconvex positive lens L7.

The positive meniscus lens L3 is the first lens and the positive meniscus lens L6 is the first lens. The biconvex positive lens L2 is the second lens and the biconvex positive lens L7 is the second lens. The negative meniscus lens L4 is the third lens and the negative meniscus lens L5 is the third lens.

In the relay optical system of the example 4, the planoconvex positive lens L1 and the planoconvex positive lens L8 are symmetrical with respect to the aperture stop S. Moreover, the cemented lens CL1 and the cemented lens CL2 are symmetrical with respect to the aperture stop S. In the relay optical system of the example 4, a symmetry plane exists at a position of the aperture stop S.

An aspheric surface is provided to a total of two surfaces which are an image-side surface of the positive meniscus lens L3 and an object-side surface of the positive meniscus lens L6.

A relay optical system of an example 5 includes in order from an object side, a planoconvex positive lens L1, a cemented lens CL1 having a positive refractive power, and a planoconvex positive lens L5. An aperture stop S is positioned at an interior of the cemented lens CL1. However, a member which restricts a light beam physically is not disposed.

The cemented lens CL1 includes a biconvex positive lens L2, a positive meniscus lens L3 having a convex surface directed toward an image side, and a negative meniscus lens L4 having a convex surface directed toward the image side.

The positive meniscus lens L3 is the first lens. The biconvex positive lens L2 is the second lens. The negative meniscus lens L4 is the third lens.

An aspheric surface is provided to an image-side surface of the positive meniscus lens L3.

A relay optical system of an example 6 includes in order from an object side, a biconvex positive lens L1, a cemented lens CL1 having a positive refractive power, a cemented lens CL2 having a positive refractive power, and a biconvex positive lens L8. An aperture stop S is disposed between the cemented lens CL1 and the cemented lens CL2.

The cemented lens CL1 includes a biconvex positive lens L2, a positive meniscus lens L3 having a convex surface directed toward an image side, and a negative meniscus lens L4 having a convex surface directed toward the image side.

The cemented lens CL2 includes a negative meniscus lens L5 having a convex surface directed toward the object side, a positive meniscus lens L6 having a convex surface directed toward the object side, and a biconvex positive lens L7.

The positive meniscus lens L3 is the first lens and the positive meniscus lens L6 is the first lens. The biconvex positive lens L2 is the second lens and the biconvex positive lens L7 is the second lens. The negative meniscus lens L4 is the third lens and the negative meniscus lens L5 is the third lens.

In the relay optical system of the example 6, the biconvex positive lens L1 and the biconvex positive lens L8 are symmetrical with respect to the aperture stop S. Moreover, the cemented lens CL1 and the cemented lens CL2 are symmetrical with respect to the aperture stop S. In the relay optical system of the example 6, a symmetry plane exists at a position of the aperture stop S.

A relay optical system of an example 7 includes in order from an object side, a planoconvex positive lens L1, a cemented lens CL1 having a positive refractive power, a cemented lens CL2 having a positive refractive power, and a planoconvex positive lens L7. An aperture stop S is disposed between the cemented lens CL1 and the cemented lens CL2.

The cemented lens CL1 includes a biconvex positive lens L2, a positive meniscus lens L3 having a convex surface directed toward an image side, and a negative meniscus lens L4 having a convex surface directed toward the image side.

The cemented lens CL2 includes a negative meniscus lens L5 having a convex surface directed toward the object side, and a biconvex positive lens L6.

The positive meniscus lens L3 is the first lens. The biconvex positive lens L2 is the second lens. The negative meniscus lens L4 is the third lens.

An aspheric surface is provided to an image-side surface of the positive meniscus lens L3.

A relay optical system of an example 8 includes in order from an object side, a planoconvex positive lens L1, a cemented lens CL1 having a positive refractive power, a cemented lens CL2 having a positive refractive power, and a planoconvex positive lens L8. An aperture stop S is disposed between the cemented lens CL1 and the cemented lens CL2.

The cemented lens CL1 includes a biconvex positive lens L2, a positive meniscus lens L3 having a convex surface directed toward an image side, and a negative meniscus lens L4 having a convex surface directed toward the image side.

The cemented lens CL2 includes a negative meniscus lens L5 having a convex surface directed toward the object side, a positive meniscus lens L6 having a convex surface directed toward the object side, and a biconvex positive lens L7.

The positive meniscus lens L3 is the first lens and the positive meniscus lens L6 is the first lens. The biconvex positive lens L2 is the second lens and the biconvex positive lens L7 is the second lens. The negative meniscus lens L4 is the third lens and the negative meniscus lens L5 is the third lens.

In the relay optical system of the example 8, the planoconvex positive lens L1 and the planoconvex positive lens L8 are symmetrical with respect to the aperture stop S. Moreover, the cemented lens CL1 and the cemented lens CL2 are symmetrical with respect to the aperture stop S. In the relay optical system of example 8, a symmetry plane exists at a position of the aperture stop S.

An aspheric surface is provided to a total of two surfaces which are an image-side surface of the positive meniscus lens L3 and an object-side surface of the positive meniscus lens L6.

A relay optical system of an example 9 includes in order from an object side, a planoconvex positive lens L1, a cemented lens CL1 having a positive refractive power, a cemented lens CL2 having a positive refractive power, and a planoconvex positive lens L8. An aperture stop S is disposed between the cemented lens CL1 and the cemented lens CL2.

The cemented lens CL1 includes a biconvex positive lens L2, a positive meniscus lens L3 having a convex surface directed toward an image side, and a negative meniscus lens L4 having a convex surface directed toward the image side.

The cemented lens CL2 includes a negative meniscus lens L5 having a convex surface directed toward the object side, a positive meniscus lens L6 having a convex surface directed the object side, and a biconvex positive lens L7.

The positive meniscus lens L3 is the first lens and the positive meniscus lens L6 is the first lens. The biconvex positive lens L2 is the second lens and the biconvex positive lens L7 is the second lens. The negative meniscus lens L4 is the third lens and the negative meniscus lens L5 is the third lens.

In the relay optical system of the example 9, the planoconvex positive lens L1 and the planoconvex positive lens L8 are symmetrical with respect to the aperture stop S. Moreover, the cemented lens CL1 and the cemented lens CL2 are symmetrical with respect to the aperture stop S. In the relay optical system of the example 9, a symmetry plane exists at a position of the aperture stop S.

An aspheric surface is provided to a total of two surfaces which are an image-side surface of the positive meniscus lens L3 and an object-side surface of the positive meniscus lens L6.

Figure 19:
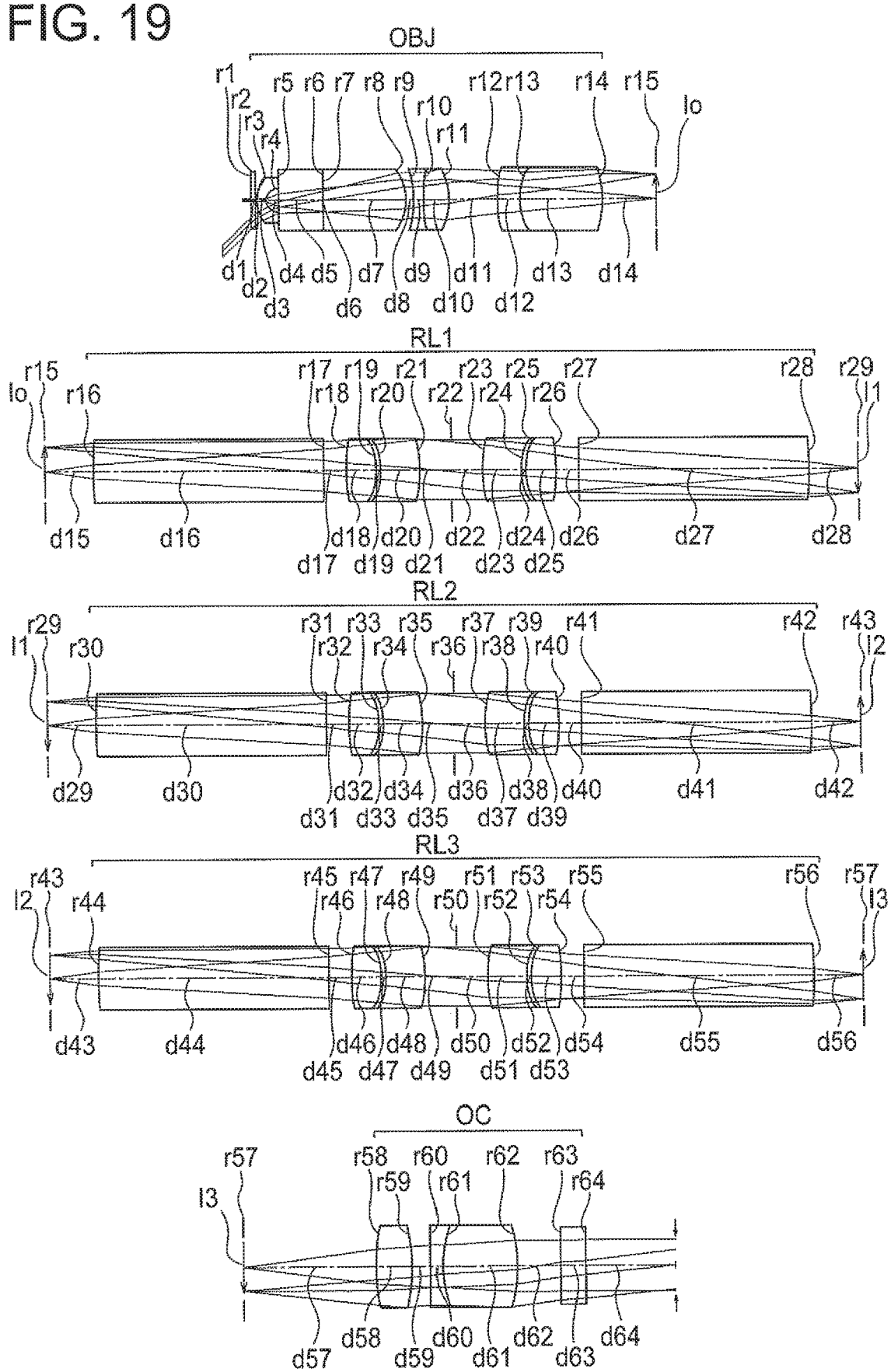
FIG. 19 is a lens cross-sectional view of an example of an optical system for rigid endoscope.

An example of an optical system for rigid endoscope will be described below. FIG. 19 is a lens cross-sectional view of the example of the optical system for rigid endoscope. FIG. 20A, FIG. 20B, FIG. 20C, and FIG. 20D are aberration diagrams of the example of the optical system for rigid endoscope.

Figure 20:
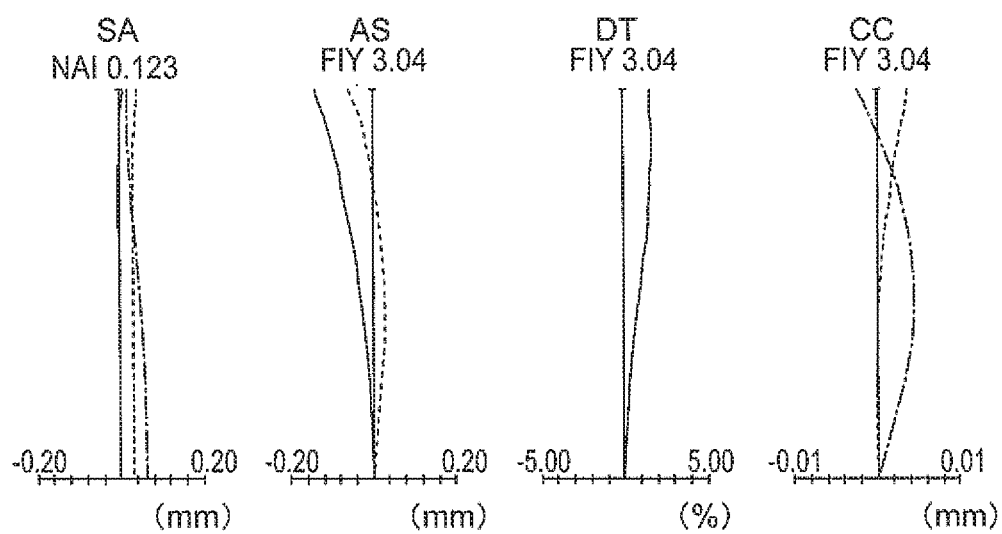
FIG. 20A, FIG. 20B, FIG. 20C, and FIG. 20D are aberration diagrams of the example of the optical system for rigid endoscope.

In the aberration diagrams, FIG. 20A shows a spherical aberration (SA), FIG. 20B shows an astigmatism (AS), FIG. 20C shows a distortion (DT), and FIG. 20D shows a chromatic aberration of magnification (CC). The aberration show an aberration when light emerged from an eyepiece optical system forms an image by an aplanatic lens. Optical specifications of the aplanatic lens are same as optical specifications of the eyepiece optical system.

The optical system for rigid endoscope of the example includes an objective optical system OBJ, an image relay unit, and an eyepiece optical system OC. The image relay unit includes a first relay optical system RL1, a second relay optical system RL2, and a third relay optical system RL3. The relay optical system of the example 1 is used for the three relay optical systems. Therefore, the description of the relay optical system will be omitted.

A primary image Io is formed by the objective optical system OBJ. The primary image Io is relayed by the first relay optical system RL1. Accordingly, a first relay image I1 is formed. The first relay image I1 is relayed by the second relay optical system RL2. Accordingly, a second relay image I2 is formed. The second relay image I2 is relayed by the third relay optical system RL3. Accordingly, a third relay image I3 is formed. It is possible to observe the third relay image I3 by the eyepiece optical system OC.

Numerical data of each example described above is shown below. In Surface data, r denotes radius of curvature of each lens surface, d denotes a distance between respective lens surfaces, nd denotes a refractive index of each lens for a d-line, vd denotes an Abbe number for each lens and * denotes an aspherical surface. LA denotes the first lens, LB denotes the second lens, and LC denotes the third lens.

Moreover, in various data, NA denotes the numerical aperture. In the examples of the relay optical system, f denotes a focal length of the relay optical system, $\theta gF_{LA}$ denotes the partial dispersion ratio, OBH denotes the maximum object height, IH denotes the maximum image height, and $\Phi_{ce}$ denotes a light-ray effective diameter. In the example of the optical system for rigid endoscope, f denotes a focal length of the optical system for rigid endoscope, co denotes a half angle of view, fOB denotes a focal length of the objective optical system, fRL denotes a focal length of the relay optical system, and fOC denotes a focal length of the eyepiece optical system.

A shape of an aspherical surface is defined by the following expression where the direction of the optical axis is represented by z, the direction orthogonal to the optical axis is represented by y, a conical coefficient is represented by K, aspherical surface coefficients are represented by A4, A6, A8, A10, A12 . . .

$$Z=(y^2/r)/[1+\{1-(1+k)(y/r)^2\}^{1/2}]+A4y^4+A6y^6+A8y^8+A10y^{10}+A12y^{12}+\ldots$$

Further, in the aspherical surface coefficients, 'e-n' (where, n is an integral number) indicates '$10^{-n}$'.

Example 1

Unit mm

Surface data

| Surface no. | r | d | nd | νd | |
|---|---|---|---|---|---|
| Object plane | ∞ | 6.03 | | | |
| 1 | 17.749 | 27.45 | 1.58913 | 61.14 | |
| 2 | ∞ | 2.78 | | | |
| 3 | 21.527 | 3.38 | 1.43875 | 94.93 | (LB) |
| 4 | −8.888 | 0.80 | 1.63387 | 23.38 | (LA) |
| 5* | −8.671 | 4.73 | 1.80625 | 40.91 | (LC) |
| 6 | −16.392 | 3.69 | | | |
| 7 (Stop) | ∞ | 3.69 | | | |
| 8 | 16.392 | 4.73 | 1.80625 | 40.91 | (LC) |
| 9* | 8.671 | 0.80 | 1.63387 | 23.38 | (LA) |
| 10 | 8.888 | 3.38 | 1.43875 | 94.93 | (LB) |
| 11 | −21.527 | 2.78 | | | |
| 12 | ∞ | 27.45 | 1.58913 | 61.14 | |
| 13 | −17.749 | 6.03 | | | |
| Image plane | ∞ | | | | |

Aspherical surface data

5th surface k = 0.000
A4 = −3.32464e−05, A6 = 5.77541e−07, A8 = −1.73224e−09

9th surface k = 0.000
A4 = 3.32464e−05, A6 = −5.77541e−07, A8 = 1.73224e−09

Various data

| f | 3132.12 |
|---|---|
| NA | 0.14 |
| θgF$_{LA}$ | 0.668 |
| OBH | 2.955 |
| IH | 2.955 |
| Φce | 7.5 |

Example 2

Unit mm

Surface data

| Surface no. | r | d | nd | νd | |
|---|---|---|---|---|---|
| Object plane | ∞ | 5.00 | | | |
| 1 | 17.933 | 30.13 | 1.58913 | 61.14 | |
| 2 | ∞ | 2.94 | | | |
| 3 | 21.755 | 2.87 | 1.49700 | 81.54 | (LB) |
| 4 | −9.683 | 0.50 | 1.63387 | 23.38 | (LA) |
| 5* | −9.136 | 4.60 | 1.80625 | 40.91 | (LC) |
| 6 | −19.780 | 2.81 | | | |
| 7(Stop) | ∞ | 2.81 | | | |
| 8 | 19.780 | 4.60 | 1.80625 | 40.91 | (LC) |
| 9* | 9.136 | 0.50 | 1.63387 | 23.38 | (LA) |
| 10 | 9.683 | 2.87 | 1.49700 | 81.54 | (LB) |
| 11 | −21.755 | 2.94 | | | |
| 12 | ∞ | 30.13 | 1.58913 | 61.14 | |
| 13 | −17.933 | 5.00 | | | |
| Image plane | ∞ | | | | |

Aspherical surface data

5th surface k = 0.000
A4 = −3.16714e−05, A6 = 3.81781e−07, A8 = 7.19077e−09

9th surface k = 0.000
A4 = 3.16714e−05, A6 = −3.81781e−07, A8 = −7.19077e−09

Various data

| f | 3204.50 |
|---|---|
| NA | 0.14 |
| θgF$_{LA}$ | 0.668 |
| OBH | 2.955 |
| IH | 2.955 |
| Φce | 7.5 |

Example 3

Unit mm

Surface data

| Surface no. | r | d | nd | νd | |
|---|---|---|---|---|---|
| Object plane | ∞ | 5.00 | | | |
| 1 | 24.434 | 34.48 | 1.69895 | 30.13 | |
| 2 | −1100.269 | 3.29 | | | |
| 3 | 28.333 | 4.67 | 1.49700 | 81.54 | (LB) |
| 4 | −7.710 | 6.00 | 1.64850 | 53.02 | (LC) |
| 5 | −24.085 | 0.80 | 1.63387 | 23.38 | (LA) |
| 6* | −21.220 | 2.52 | | | |
| 7(Stop) | ∞ | 2.52 | | | |
| 8* | 21.220 | 0.80 | 1.63387 | 23.38 | (LA) |
| 9 | 24.085 | 6.00 | 1.64850 | 53.02 | (LC) |
| 10 | 7.710 | 4.67 | 1.49700 | 81.54 | (LB) |
| 11 | −28.333 | 3.29 | | | |
| 12 | 1100.269 | 34.48 | 1.69895 | 30.13 | |
| 13 | −24.434 | 5.00 | | | |
| Image plane | ∞ | | | | |

Aspherical surface data

6th surface k = 0.000
A4 = −6.32197e−06, A6 = −1.03462e−07, A8 = −1.28546e−09

8th surface k = 0.000
A4 = 6.32197e−06, A6 = 1.03462e−07, A8 = 1.28546e−09

Various data

| f | 4279.87 |
|---|---|
| NA | 0.12 |
| θgF$_{LA}$ | 0.668 |
| OBH | 2.955 |
| IH | 2.955 |
| Φce | 7.5 |

Example 4

Unit mm

Surface data

| Surface no. | r | d | nd | νd | |
|---|---|---|---|---|---|
| Object plane | ∞ | 5.00 | | | |
| 1 | 17.449 | 33.69 | 1.58913 | 61.14 | |
| 2 | ∞ | 2.38 | | | |
| 3 | 19.258 | 2.23 | 1.51633 | 64.14 | (LB) |

-continued

Unit mm

| | | | | | |
|---|---|---|---|---|---|
| 4 | −10.902 | 0.50 | 1.63387 | 23.38 | (LA) |
| 5* | −8.243 | 3.03 | 1.90270 | 31.00 | (LC) |
| 6 | −19.416 | 2.02 | | | |
| 7(Stop) | ∞ | 2.02 | | | |
| 8 | 19.416 | 3.03 | 1.90270 | 31.00 | (LC) |
| 9* | 8.243 | 0.50 | 1.63387 | 23.38 | (LA) |
| 10 | 10.902 | 2.23 | 1.51633 | 64.14 | (LB) |
| 11 | −19.258 | 2.38 | | | |
| 12 | ∞ | 33.69 | 1.58913 | 61.14 | |
| 13 | −17.449 | 5.00 | | | |
| Image plane | ∞ | | | | |

Aspherical surface data

5th surface k = 0.000
A4 = 2.05320e−05, A6 = 1.31245e−06, A8 = −2.73124e−08

9th surface k = 0.000
A4 = −2.05320e−05, A6 = −1.31245e−06, A8 = 2.73124e−08

Various data

| | |
|---|---|
| f | 2912.93 |
| NA | 0.09 |
| $\theta gF_{LA}$ | 0.668 |
| OBH | 2.955 |
| IH | 2.955 |
| Φce | 5.669854 |

Example 5

Unit mm

Surface data

| Surface no. | r | d | nd | vd | |
|---|---|---|---|---|---|
| Object plane | ∞ | 5.00 | | | |
| 1 | 18.172 | 24.09 | 1.58913 | 61.14 | |
| 2 | ∞ | 11.53 | | | |
| 3 | 8.215 | 11.03 | 1.43875 | 94.93 | (LB) |
| 4(Stop) | ∞ | 0.00 | 1.43875 | 94.93 | |
| 5 | −5.097 | 0.50 | 1.63387 | 23.38 | (LA) |
| 6* | −4.713 | 4.93 | 1.80625 | 40.91 | (LC) |
| 7 | −11.130 | 11.53 | | | |
| 8 | ∞ | 24.09 | 1.58913 | 61.14 | |
| 9 | −18.172 | 5.00 | | | |
| Image plane | ∞ | | | | |

Aspherical surface data

6th surface k = 0.000
A4 = −1.85896e−04, A6 = 2.18965e−05, A8 = 1.25570e−06

Various data

| | |
|---|---|
| f | −144.82 |
| NA | 0.08 |
| $\theta gF_{LA}$ | 0.668 |
| OBH | 2.955 |
| IH | 2.955 |
| Φce | 6.6423 |

Example 6

Unit mm

Surface data

| Surface no. | r | d | nd | vd | |
|---|---|---|---|---|---|
| Object plane | ∞ | 5.00 | | | |
| 1 | 20.297 | 33.84 | 1.69895 | 30.13 | |
| 2 | −54.889 | 0.65 | | | |
| 3 | 21.275 | 3.82 | 1.49700 | 81.54 | (LB) |
| 4 | −11.733 | 0.80 | 1.63387 | 23.38 | (LA) |
| 5 | −10.985 | 2.70 | 1.88300 | 40.76 | (LC) |
| 6 | −25.624 | 2.05 | | | |
| 7(Stop) | ∞ | 2.05 | | | |
| 8 | 25.624 | 2.70 | 1.88300 | 40.76 | (LC) |
| 9 | 10.985 | 0.80 | 1.63387 | 23.38 | (LA) |
| 10 | 11.733 | 3.82 | 1.49700 | 81.54 | (LB) |
| 11 | −21.275 | 0.65 | | | |
| 12 | 54.889 | 33.84 | 1.69895 | 30.13 | |
| 13 | −20.297 | 5.00 | | | |
| Image plane | ∞ | | | | |

Various data

| | |
|---|---|
| f | 3183.08 |
| NA | 0.10 |
| $\theta gF_{LA}$ | 0.668 |
| OBH | 2.955 |
| IH | 2.955 |
| Φce | 5.94823 |

Example 7

Unit mm

Surface data

| Surface no. | r | d | nd | vd | |
|---|---|---|---|---|---|
| Object plane | ∞ | 4.00 | | | |
| 1 | 20.911 | 17.27 | 1.58913 | 61.14 | |
| 2 | ∞ | 13.30 | | | |
| 3 | 20.798 | 7.26 | 1.43875 | 94.93 | (LB) |
| 4 | −9.808 | 0.80 | 1.63387 | 23.38 | (LA) |
| 5* | −8.934 | 4.90 | 1.80625 | 40.91 | (LC) |
| 6 | −18.011 | 1.73 | | | |
| 7(Stop) | ∞ | 1.73 | | | |
| 8 | 18.011 | 4.90 | 1.80625 | 40.91 | |
| 9 | 9.808 | 7.26 | 1.43875 | 94.93 | |
| 10 | −20.798 | 13.30 | | | |
| 11 | ∞ | 17.27 | 1.58913 | 61.14 | |
| 12 | −20.911 | 4.00 | | | |
| Image plane | ∞ | | | | |

Aspherical surface data

5th surface k = 0.000
A4 = −5.29386e−05, A6 = 2.57264e−07, A8 = 4.07438e−08

Various data

| | |
|---|---|
| f | −5183.95 |
| NA | 0.10 |
| $\theta gF_{LA}$ | 0.668 |
| OBH | 2.955 |
| IH | 2.955 |
| Φce | 6.75044 |

Example 8

Unit mm

Surface data

| Surface no. | r | d | nd | νd | |
|---|---|---|---|---|---|
| Object plane | ∞ | 5.33 | | | |
| 1 | 18.247 | 27.82 | 1.58913 | 61.14 | |
| 2 | ∞ | 3.23 | | | |
| 3 | 21.047 | 3.30 | 1.43875 | 94.93 | (LB) |
| 4 | −9.083 | 0.80 | 1.62060 | 25.97 | (LA) |
| 5* | −8.632 | 4.46 | 1.80625 | 40.91 | (LC) |
| 6 | −16.312 | 3.91 | | | |
| 7(Stop) | ∞ | 3.91 | | | |
| 8 | 16.312 | 4.46 | 1.80625 | 40.91 | (LC) |
| 9* | 8.632 | 0.80 | 1.62060 | 25.97 | (LA) |
| 10 | 9.083 | 3.30 | 1.43875 | 94.93 | (LB) |
| 11 | −21.047 | 3.23 | | | |
| 12 | ∞ | 27.82 | 1.58913 | 61.14 | |
| 13 | −18.247 | 5.33 | | | |
| Image plane | ∞ | | | | |

Aspherical surface data

5th surface k = 0.000
A4 = −3.54882e−05, A6 = 4.06157e−07, A8 = 2.27961e−09

9th surface k = 0.000
A4 = 3.54882e−05, A6 = −4.06157e−07, A8 = −2.27961e−09

Various data

| f | 3306.71 |
|---|---|
| NA | 0.14 |
| θgF$_{LA}$ | 0.628 |
| OBH | 2.955 |
| IH | 2.955 |
| Φce | 7.5 |

Example 9

Unit mm

Surface data

| Surface no. | r | d | nd | νd | |
|---|---|---|---|---|---|
| Object plane | ∞ | 6.40 | | | |
| 1 | 18.250 | 25.30 | 1.58913 | 61.14 | |
| 2 | ∞ | 3.33 | | | |
| 3 | 25.494 | 3.08 | 1.43875 | 94.93 | (LB) |
| 4 | −8.681 | 0.80 | 1.63598 | 23.46 | (LA) |
| 5* | −8.828 | 4.43 | 1.80625 | 40.91 | (LC) |
| 6 | −15.460 | 5.51 | | | |
| 7(Stop) | ∞ | 5.51 | | | |
| 8 | 15.460 | 4.43 | 1.80625 | 40.91 | (LC) |
| 9* | 8.828 | 0.80 | 1.63598 | 23.46 | (LA) |
| 10 | 8.681 | 3.08 | 1.43875 | 94.93 | (LB) |
| 11 | −25.494 | 3.33 | | | |
| 12 | ∞ | 25.30 | 1.58913 | 61.14 | |
| 13 | −18.250 | 6.40 | | | |
| Image plane | ∞ | | | | |

Aspherical surface data

5th surface k = 0.000
A4 = −3.54739e−05, A6 = −2.01973e−07, A8 = 3.74445e−08

9th surface k = 0.000
A4 = 3.54739e−05, A6 = 2.01973e−07, A8 = −3.74445e−08

Various data

| f | 3470.24 |
|---|---|
| NA | 0.11 |
| θgF$_{LA}$ | 0.8 |
| OBH | 2.955 |
| IH | 2.955 |
| Φce | 7.34 |

Example 10

Unit mm

Surface data

| Surface no. | r | d | nd | νd |
|---|---|---|---|---|
| Object plane | ∞ | 50.00 | | |
| 1 | ∞ | 0.70 | 1.76900 | 64.15 |
| 2 | ∞ | 0.20 | | |
| 3* | 4.245 | 0.93 | 1.80610 | 40.92 |
| 4* | 1.011 | 1.46 | | |
| 5 | ∞ | 5.25 | 1.80610 | 40.95 |
| 6 | ∞ | 0.00 | 1.80610 | 40.92 |
| 7 | ∞ | 10.01 | 1.80610 | 40.92 |
| 8* | −6.225 | 0.96 | | |
| 9 | −20.942 | 1.34 | 1.83400 | 37.16 |
| 10 | 15.378 | 3.00 | 1.49700 | 81.54 |
| 11 | −7.897 | 5.82 | | |
| 12 | 22.118 | 2.66 | 1.84666 | 23.78 |
| 13 | 6.545 | 9.64 | 1.49700 | 81.54 |
| 14 | −14.451 | 6.68 | | |
| 15 | ∞ | 6.03 | | |
| 16 | 17.749 | 27.45 | 1.58913 | 61.14 |
| 17 | ∞ | 2.78 | | |
| 18 | 21.527 | 3.38 | 1.43875 | 94.93 |
| 19 | −8.888 | 0.80 | 1.63387 | 23.38 |
| 20* | −8.671 | 4.73 | 1.80625 | 40.91 |
| 21 | −16.392 | 3.69 | | |
| 22 | ∞ | 3.69 | | |
| 23 | 16.392 | 4.73 | 1.80625 | 40.91 |
| 24* | 8.671 | 0.80 | 1.63387 | 23.38 |
| 25 | 8.888 | 3.38 | 1.43875 | 94.93 |
| 26 | −21.527 | 2.78 | | |
| 27 | ∞ | 27.45 | 1.58913 | 61.14 |
| 28 | −17.749 | 6.03 | | |
| 29 | ∞ | 6.03 | | |
| 30 | 17.749 | 27.45 | 1.58913 | 61.14 |
| 31 | ∞ | 2.78 | | |
| 32 | 21.527 | 3.38 | 1.43875 | 94.93 |
| 33 | −8.888 | 0.80 | 1.63387 | 23.38 |
| 34* | −8.671 | 4.73 | 1.80625 | 40.91 |
| 35 | −16.392 | 3.69 | | |
| 36 | ∞ | 3.69 | | |
| 37 | 16.392 | 4.73 | 1.80625 | 40.91 |
| 38* | 8.671 | 0.80 | 1.63387 | 23.38 |
| 39 | 8.888 | 3.38 | 1.43875 | 94.93 |
| 40 | −21.527 | 2.78 | | |
| 41 | ∞ | 27.45 | 1.58913 | 61.14 |
| 42 | −17.749 | 6.03 | | |
| 43 | ∞ | 6.03 | | |
| 44 | 17.749 | 27.45 | 1.58913 | 61.14 |
| 45 | ∞ | 2.78 | | |
| 46 | 21.527 | 3.38 | 1.43875 | 94.93 |
| 47 | −8.888 | 0.80 | 1.63387 | 23.38 |
| 48* | −8.671 | 4.73 | 1.80625 | 40.91 |
| 49 | −16.392 | 3.69 | | |
| 50 | ∞ | 3.69 | | |

-continued

Unit mm

| | | | | |
|---|---|---|---|---|
| 51 | 16.392 | 4.73 | 1.80625 | 40.91 |
| 52* | 8.671 | 0.80 | 1.63387 | 23.38 |
| 53 | 8.888 | 3.38 | 1.43875 | 94.93 |
| 54 | −21.527 | 2.78 | | |
| 55 | ∞ | 27.45 | 1.58913 | 61.14 |
| 56 | −17.749 | 6.03 | | |
| 57 | ∞ | 16.18 | | |
| 58 | 33.647 | 4.14 | 1.43875 | 94.93 |
| 59 | −23.882 | 2.17 | | |
| 60 | 224.243 | 1.49 | 1.83400 | 37.16 |
| 61 | 13.762 | 8.87 | 1.58913 | 61.14 |
| 62 | −19.905 | 5.36 | | |
| 63 | ∞ | 3.00 | 1.76819 | 71.70 |
| 64 | ∞ | 10.50 | | |
| Pupil plane | ∞ | | | |

Aspherical surface data

3rd surface k = 0.114
A4 = −8.32004e-03, A6 = 1.91171e-04

4th surface k = −0.770
A4 = −6.47508e-03, A6 = −7.26821e-03

8th surface k = −0.710
A4 = 2.04648e-04, A6 = −5.61088e-07

20th surface k = 0.000
A4 = −3.32464e-05, A6 = 5.77541e-07, A8 = −1.73224e-09

24th surface k = 0.000
A4 = 3.32464e-05, A6 = −5.77541e-07, A8 = 1.73224e-09

34th surface k = 0.000
A4 = −3.32464e-05, A6 = 5.77541e-07, A8 = −1.73224e-09

38th surface k = 0.000
A4 = 3.32464e-05, A6 = −5.77541e-07, A8 = 1.73224e-09

48th surface k = 0.000
A4 = −3.32464e-05, A6 = 5.77541e-07, A8 = −1.73224e-09

52th surface k = 0.000
A4 = 3.32464e-05, A6 = −5.77541e-07, A8 = 1.73224e-09

Various data

| | |
|---|---|
| f | 3.13 |
| NA | 0.12 |
| 2ω | 87.19 |
| fOB | 3.07 |
| fRL | 1044.04 |
| fOC | 23.30 |

The values of conditional expressions (1) to (7) in each example are shown below.

| | Example1 | Example2 | Example3 | Example4 |
|---|---|---|---|---|
| (1)$\beta_{LA}$ | 0.71 | 0.71 | 0.71 | 0.71 |
| (2)$vd_{LA}$ | 23.38 | 23.38 | 23.38 | 23.38 |
| (3)mg | 1.0 | 1.0 | 1.0 | 1.0 |
| (4)\|(R1 − R2)/(R1 + R2)\| | 0.01 | 0.03 | 0.06 | 0.14 |
| (5)$nd_{LB}$ | 1.43875 | 1.497 | 1.497 | 1.51633 |
| (6)$vd_{LB}$ | 94.93 | 81.54 | 81.54 | 64.14 |
| (7)(OBH + IH)/Φce | 0.79 | 0.79 | 0.79 | 1.04 |

| | Example5 | Example6 | Example 7 | Example8 |
|---|---|---|---|---|
| (1)$\beta_{LA}$ | 0.71 | 0.71 | 0.71 | 0.67 |
| (2)$vd_{LA}$ | 23.38 | 23.38 | 23.38 | 25.97 |
| (3)mg | 1.0 | 1.0 | 1.0 | 1.0 |
| (4)\|(R1 − R2)/(R1 + R2)\| | 0.04 | 0.03 | 0.05 | 0.03 |
| (5)$nd_{LB}$ | 1.43875 | 1.497 | 1.43875 | 1.43875 |
| (6)$vd_{LB}$ | 94.93 | 81.54 | 94.93 | 94.93 |
| (7)(OBH + IH)/Φce | 0.89 | 0.99 | 0.88 | 0.79 |

| | Example9 |
|---|---|
| (1)$\beta_{LA}$ | 0.84 |
| (2)$vd_{LA}$ | 23.468 |
| (3)mg | 1.0 |
| (4)\|(R1 − R2)/(R1 + R2)\| | 0.01 |
| (5)$nd_{LB}$ | 1.43875 |
| (6)$vd_{LB}$ | 94.93 |
| (7)(OBH + IH)/Φce | 0.81 |

Figure 21:
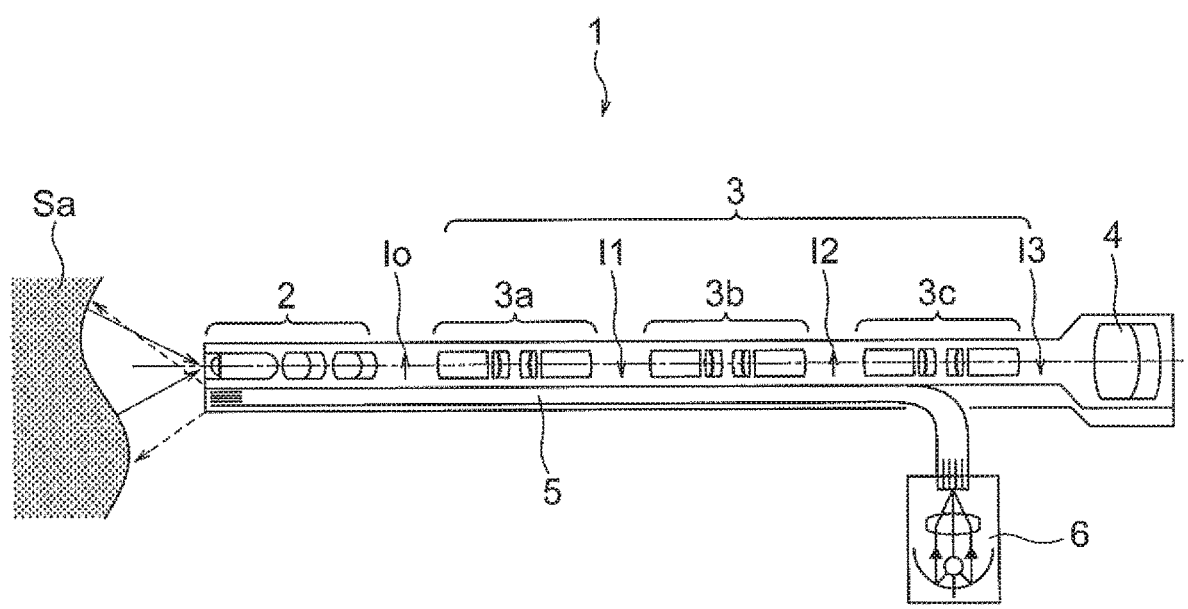
FIG. 21 is a schematic structural view of a rigid endoscope.

An example of a rigid endoscope will be described below. FIG. 21 is a schematic structural view of the rigid endoscope. A rigid endoscope 1 includes an objective optical system 2, an image relay unit 3, and an eyepiece optical system 4. Furthermore, the rigid endoscope 1 includes alight guide 5 and an illuminating-unit light source 6.

The image relay unit 3 includes a first relay optical system 3a, a second relay optical system 3b, and a third relay optical system 3c. The relay optical system of the example 1 is used for three relay optical systems.

Illuminating light is emerged from the illuminating-unit light source 6. The illuminating light, upon passing through the light guide 5, is emerged from a front end of the rigid endoscope. Accordingly, the illuminating light is irradiated to an observation object Sa.

A primary image Io of the observation object Sa is formed by the objective optical system 1. The primary image Io is relayed by the first relay optical system 3a. Accordingly, a first relay image I1 is formed. The first relay image I1 is relayed by the second relay optical system 3b. Accordingly, a second relay image I2 is formed. The second relay image I2 is relayed by the third relay optical system 3c. Accordingly, a third relay image I3 is formed. It is possible to observe the third relay image I3 by the eyepiece optical system OC.

Figure 22A:
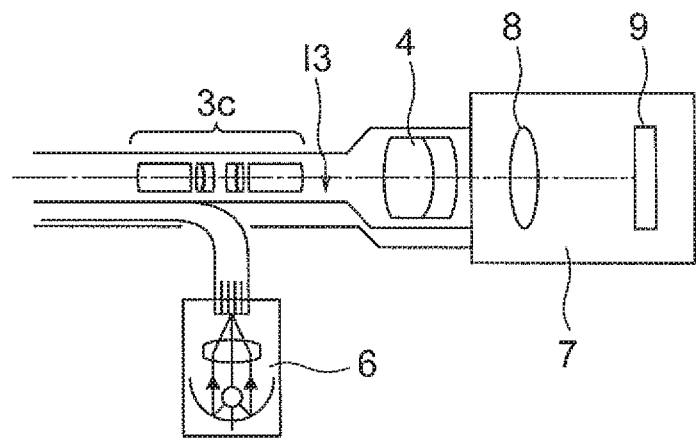
FIG. 22A and FIG. 22B are schematic structural views of an image pickup apparatus.
Figure 22B:
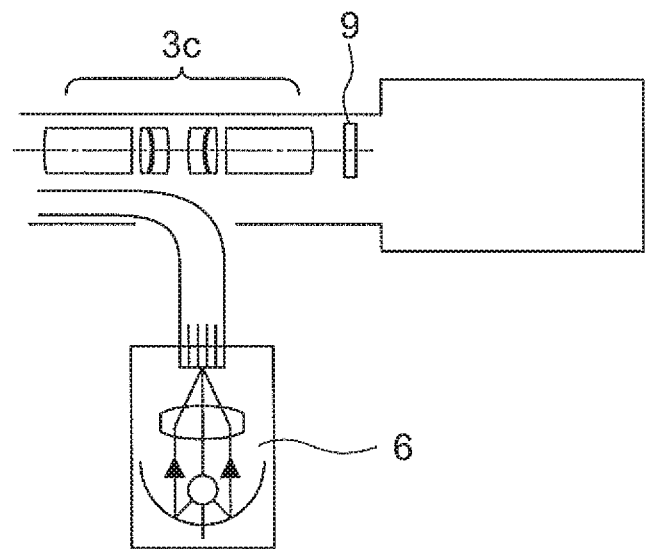

It is possible to capture the third relay image I3 by an image pickup element. FIG. 22A and FIG. 22B are schematic structural views of an image pickup apparatus. FIG. 22A shows an arrangement for capturing via the eyepiece optical system. FIG. 22B shows an arrangement for capturing without passing through the eyepiece optical system.

In the arrangement for capturing passing through the eyepiece optical system, an image pickup unit 7 includes an image forming lens 8 and an image pickup element 9. By the eyepiece optical system 4 and the image forming lens 8, an image of the third relay image I3 is formed on an image pickup surface of the image pickup element 9. By capturing the image by the image pickup element 9, it is possible to acquire an image of the observation object Sa.

In the arrangement for capturing without passing through the eyepiece optical system, the image pickup unit 7 includes the image pickup element 9. The third relay image I3 is formed on an image pickup surface of the image pickup element 9. By capturing the image by the image pickup element 9, it is possible to acquire an image of the observation object Sa.

According to the present embodiment, it is possible to provide a relay optical system in which the chromatic aberration is corrected favorably, and an optical system for rigid endoscope and a rigid endoscope in which the relay optical system is used.

As described heretofore, the present invention is suitable for a relay optical system in which the chromatic aberration is corrected favorably, and an optical system for rigid endoscope and a rigid endoscope in which the relay optical system is used.

What is claimed is:

1. A relay optical system, comprising:
a cemented lens in which a first lens having a positive refractive power, a second lens having a positive refractive power, and a third lens having a negative refractive power are cemented,
wherein:
the cemented lens is disposed in an optical path of the relay optical system, which is formed by an object-side optical path and an image-side optical path, and
the first lens is a meniscus lens which is adjacent to the third lens,
a dispersion and a partial dispersion ratio differ for the first lens and the third lens,
in a rectangular coordinate system in which a horizontal axis is set to be $vd_{LA}$ and a vertical axis is set to be $\theta gF_{LA}$,
when a straight line expressed by $\theta gF_{LA} = \alpha \times vd_{LA} + \beta_{LA}$ is set, where $\alpha = -0.00163$,
$\theta gF_{LA}$ and $vd_{LA}$ of a medium of the first lens are included in an area determined by the following conditional expression (1) and conditional expression (2), and
the following conditional expression (3) is satisfied:

$$0.67 \leq \beta_{LA} \quad (1)$$

$$vd_{LA} < 50 \quad (2)$$

$$-1.4 < mg < -0.6 \quad (3)$$

where,
$\theta gF_{LA}$ denotes a partial dispersion ratio $(ng_{LA}-nF_{LA})/(nF_{LA}-nC_{LA})$ of the medium of the first lens,
$vd_{LA}$ denotes Abbe number $(nd_{LA}-1)/(nF_{LA}-nC_{LA})$ for the medium of the first lens,
$nd_{LA}$, $nC_{LA}$, $nF_{LA}$, and $ng_{LA}$ are refractive indices of the medium of the first lens for a d-line, a C-line, an F-line, and a g-line respectively,
mg denotes a magnification of the relay optical system,
the object-side optical path is an optical path positioned on an object side of a center of the relay optical system, and
the image-side optical path is an optical path positioned on an image side of the center of the relay optical system.

2. The relay optical system according to claim 1, wherein the first lens is positioned between the second lens and the third lens.

3. The relay optical system according to claim 1, wherein the third lens is positioned between the second lens and the first lens.

4. The relay optical system according to claim 1, wherein the first lens is a resin lens.

5. The relay optical system according to claim 1, wherein the following conditional expression (4) is satisfied:

$$0 < |(R1-R2)/(R1+R2)| < 3 \quad (4)$$

where,
R1 denotes a radius of curvature of an object side of the first lens, and
R2 denotes a radius of curvature of an image side of the first lens.

6. The relay optical system according to claim 1, wherein the following conditional expressions (5) and (6) are satisfied:

$$1.4 < nd_{LB} < 1.6 \quad (5)$$

$$50 < vd_{LB} < 100 \quad (6)$$

where,
$nd_{LB}$ denotes a refractive index of a medium of the second lens for the d-line,
$vd_{LB}$ denotes Abbe number $(nd_{LB}-1)/(nF_{LB}-nC_{LB})$ for the medium of the second lens, and
$nd_{LB}$, $nC_{LB}$, $nF_{LB}$, and $ng_{LB}$ are refractive indices of the medium of the second lens for the d-line, the C-line, the F-line, and the g-line.

7. The relay optical system according to claim 1, wherein the cemented lens is disposed in at least one of the object-side optical path and the image-side optical path.

8. The relay optical system according to claim 1, wherein the cemented lens is disposed in each of the object-side optical path and the image-side optical path.

9. The relay optical system according to claim 1, wherein the relay optical system includes at least one aspheric surface.

10. The relay optical system according to claim 1, comprising:
an object-side lens which is disposed in the object-side optical path; and
an image-side lens which is disposed in the image-side optical path,
wherein:
the object-side lens has a positive refractive power, and is disposed such that a convex surface is directed toward the object side,
the image-side lens has a positive refractive power, and is disposed such that a convex surface is directed toward the image side, and
the cemented lens is disposed between the object-side lens and the image-side lens.

11. The relay optical system according to claim 1, wherein:
a lens surface positioned nearest to image in the object-side optical path is a surface which is convex toward the image side, and
a lens surface positioned nearest to object in the image-side optical path is a surface which is convex toward the object side.

12. The relay optical system according to claim 1, wherein the following conditional expression (7) is satisfied:

$$0.2 < (OBH+IH)/\Phi ce < 1.8 \quad (7)$$

where,
$\Phi ce$ denotes a light-ray effective diameter of the cemented lens,
OBH denotes a maximum object height, and
IH denotes a maximum image height.

13. An image relay unit, comprising:
a plurality of relay optical systems,
wherein at least one relay optical system of the plurality of relay optical systems is the relay optical system according to claim 1.

14. An optical system for rigid endoscope, comprising:
an objective optical system; and
an image relay unit which is disposed on an image side of the objective optical system,
wherein the image relay unit is the image relay unit according to claim 13.

15. The optical system for rigid endoscope according to claim 14, comprising:
an eyepiece optical system which is disposed on an image side of the image relay unit.

16. A rigid endoscope, comprising:
the optical system for rigid endoscope according to claim 14; and
an image pickup element which captures an image formed by the image relay unit.

17. A rigid endoscope, comprising:
the optical system for rigid endoscope according to claim 15; and
an illuminating unit which illuminates an object to be observed.

18. The rigid endoscope according to claim 16, comprising:
an illuminating unit for illuminating an object to be observed.

* * * * *